(12) United States Patent
O'Neil et al.

(10) Patent No.: US 9,339,525 B2
(45) Date of Patent: May 17, 2016

(54) INHIBITION OF BIOFILM ORGANISMS

(75) Inventors: Deborah O'Neil, Aberdeen (GB); Derry Mercer, Aberdeen (GB); Cedric Charrier, Aberdeen (GB)

(73) Assignee: Novabiotics Limited, Aberdeen (GB)

( * ) Notice: Subject to any disclaimer, the term of this patent is extended or adjusted under 35 U.S.C. 154(b) by 795 days.

(21) Appl. No.: 13/260,547

(22) PCT Filed: Mar. 31, 2010

(86) PCT No.: PCT/GB2010/000631
§ 371 (c)(1),
(2), (4) Date: Nov. 17, 2011

(87) PCT Pub. No.: WO2010/112848
PCT Pub. Date: Oct. 7, 2010

(65) Prior Publication Data
US 2012/0189682 A1    Jul. 26, 2012

Related U.S. Application Data

(60) Provisional application No. 61/165,396, filed on Mar. 31, 2009.

(30) Foreign Application Priority Data

Mar. 31, 2009   (GB) .................................. 0905451.1

(51) Int. Cl.
| A61K 38/00 | (2006.01) |
| --- | --- |
| A61K 38/02 | (2006.01) |
| A61K 38/08 | (2006.01) |
| A61K 31/145 | (2006.01) |
| A61K 38/17 | (2006.01) |
| A61L 15/44 | (2006.01) |
| A61L 15/46 | (2006.01) |
| A61L 27/54 | (2006.01) |
| A61L 29/16 | (2006.01) |
| A61L 31/16 | (2006.01) |

(52) U.S. Cl.
CPC .............. *A61K 38/08* (2013.01); *A61K 31/145* (2013.01); *A61K 38/1729* (2013.01); *A61L 15/44* (2013.01); *A61L 15/46* (2013.01); *A61L 27/54* (2013.01); *A61L 29/16* (2013.01); *A61L 31/16* (2013.01); *A61L 2300/254* (2013.01); *A61L 2300/404* (2013.01); *A61L 2300/424* (2013.01); *A61L 2300/45* (2013.01)

(58) Field of Classification Search
CPC ............................... A61K 38/00; A61K 3/028
See application file for complete search history.

(56) References Cited

U.S. PATENT DOCUMENTS

| 3,991,190 | A | * | 11/1976 | Garzia et al. | ................... 514/275 |
| --- | --- | --- | --- | --- | --- |
| 8,415,398 | B2 | * | 4/2013 | Liang et al. | ................... 514/665 |
| 2006/0140906 | A1 | * | 6/2006 | Chi et al. | ..................... 424/85.2 |
| 2007/0244044 | A1 | * | 10/2007 | O'Neil | ........................... 514/12 |

FOREIGN PATENT DOCUMENTS

| WO | WO 2007/050565 A2 | 3/2007 |
| --- | --- | --- |
| WO | WO 2008/093058 A2 | 7/2008 |

OTHER PUBLICATIONS

Aaron et al. Eur Respir J 2004; 24: 631-637.*
Beckloff, N. et al., "Activity of an Antimicrobial Peptide Mimetic Against Planktonic and Biofilm cultures of Oral Pathogens," Antimicrobial Gents and Chemotherapy, vol. 51, No. 11, p. 4125-4132 (2007).
Jayaraman A., et al., "Inhibiting Sulfate-Reducing Bacteria in Biofilms by Expressing the Antimicrobial Peptides Indolicidin and Bactenecin," J. of Industrial Microbiology and Biotechnology, vol. 22, p. 167-175, (1999).
Oosterhof, J.J.H., et al., "The Influence of Antimicrobial Peptides and Mucolytics on the Integrity of Biofilms Consisting of Bacteria and Yeasts as Affecting Voice Prosthetic Air Flow Resistances," Biofouling (Chur), vol. 19, No. 6, p. 347-353, (2003).

* cited by examiner

*Primary Examiner* — Karlheinz R Skowronek
*Assistant Examiner* — Li Lee
(74) *Attorney, Agent, or Firm* — Morgan, Lewis & Bockius LLP

(57) ABSTRACT

The present invention relates to a product comprising at least two antibiofilm agents wherein at least one of the antibiofilm agents is an antimicrobial peptide. The second antibiofilm agent is cysteamine. There is also provided the use of the product in the treatment of a microbial infection.

15 Claims, 30 Drawing Sheets

Figure 14
(a)
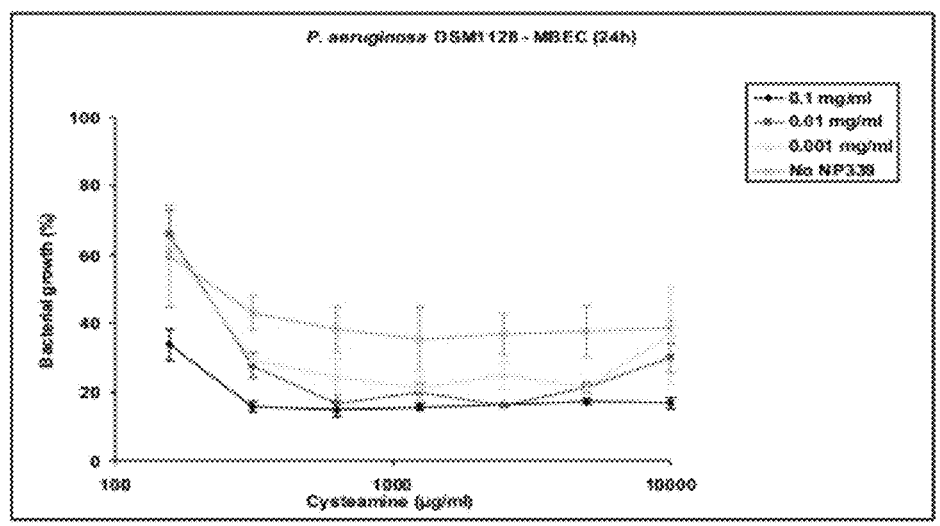
(b)
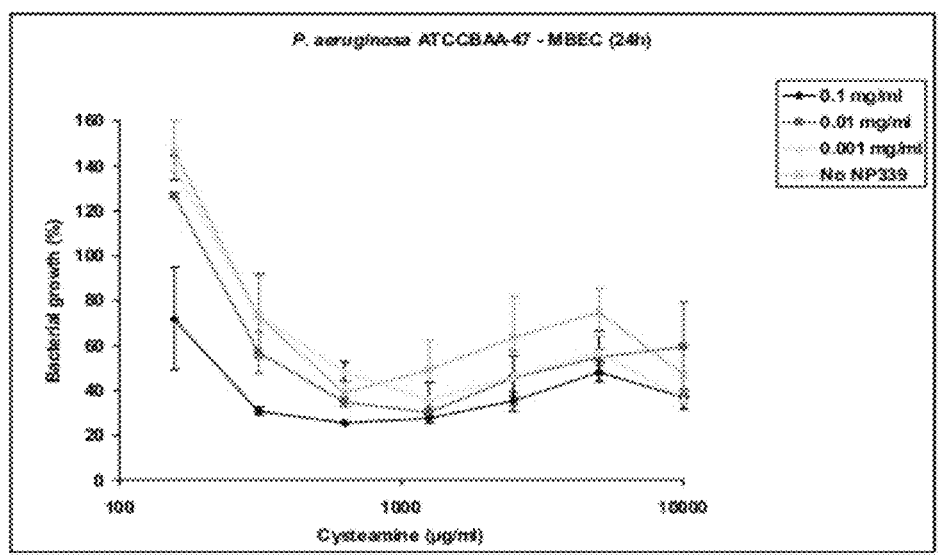

Figure 14 Cont.
(c)
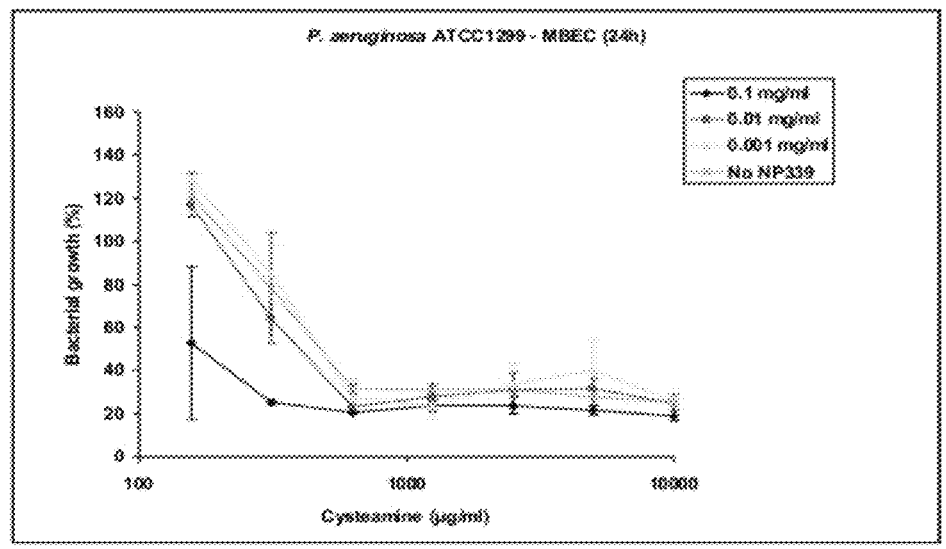
(d)
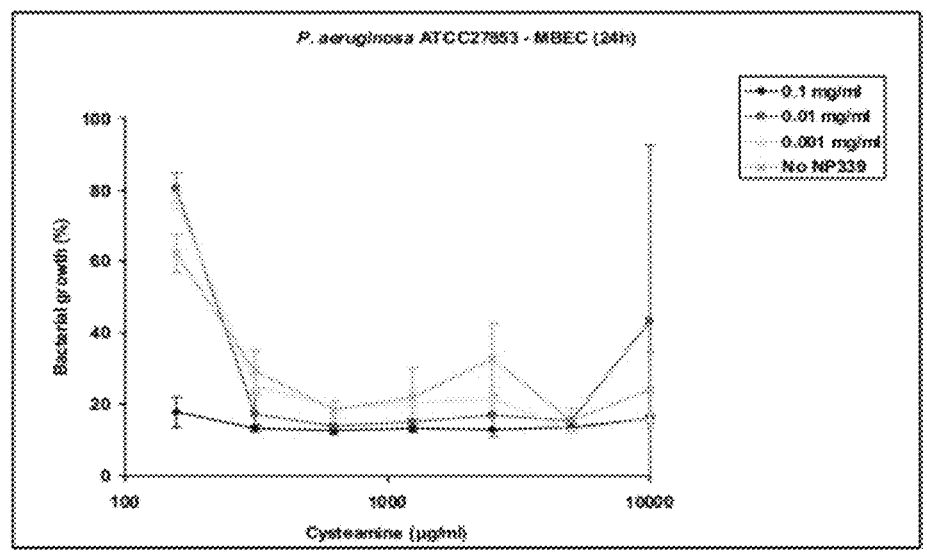

Figure 15
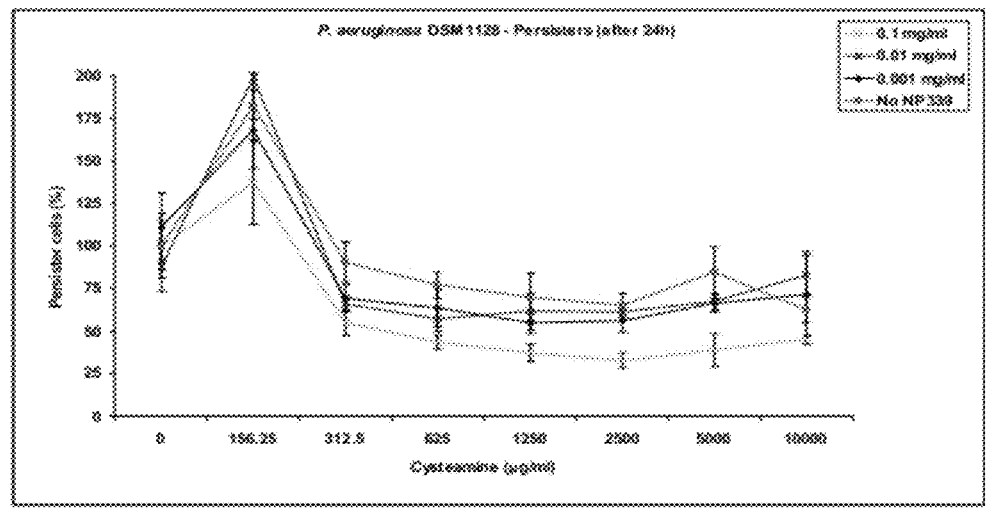
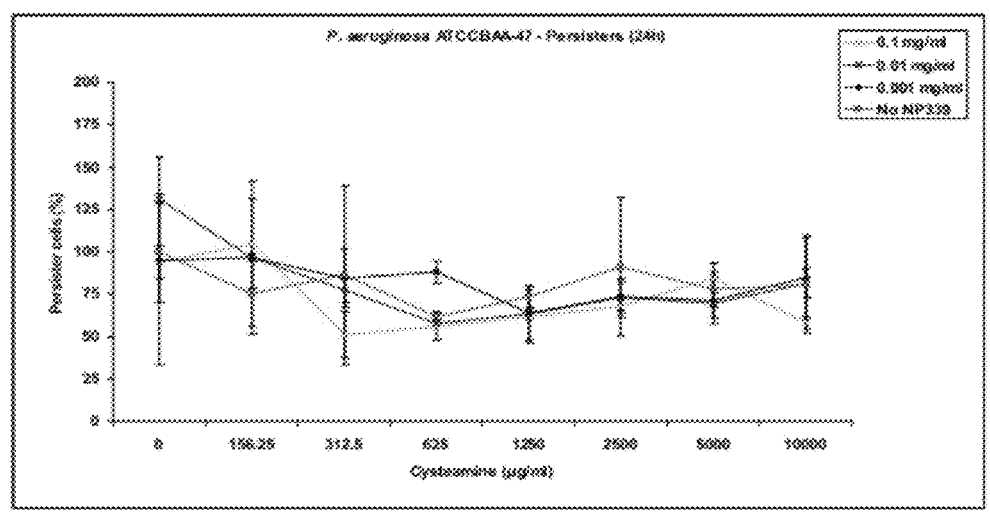

Figure 20
(a)
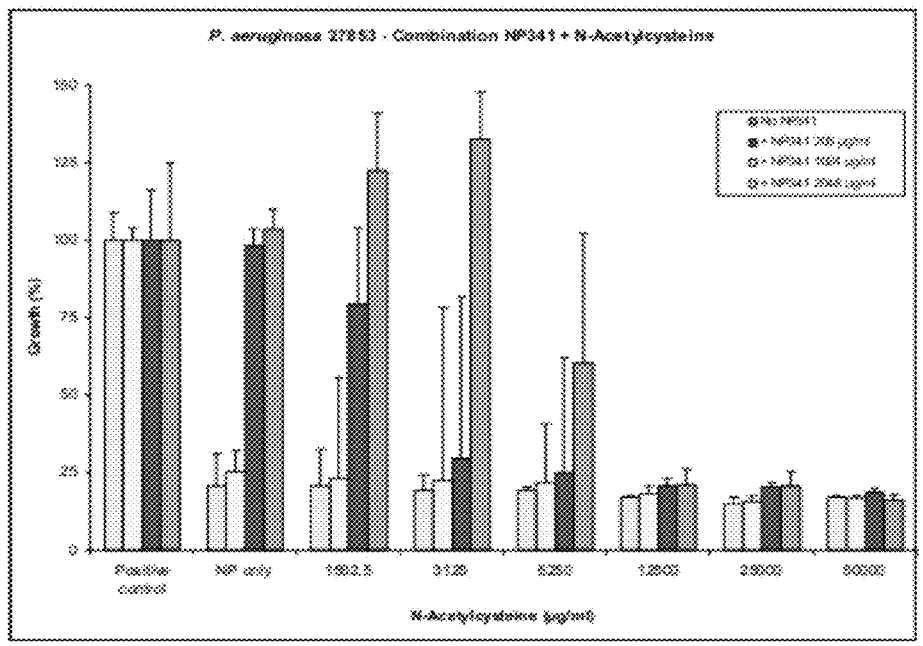
(b)
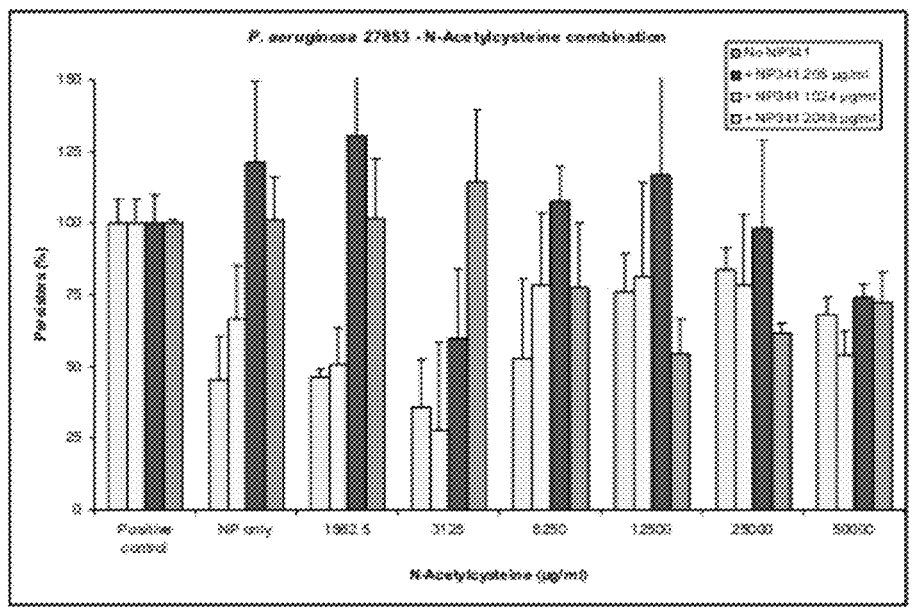

Figure 21
(a)
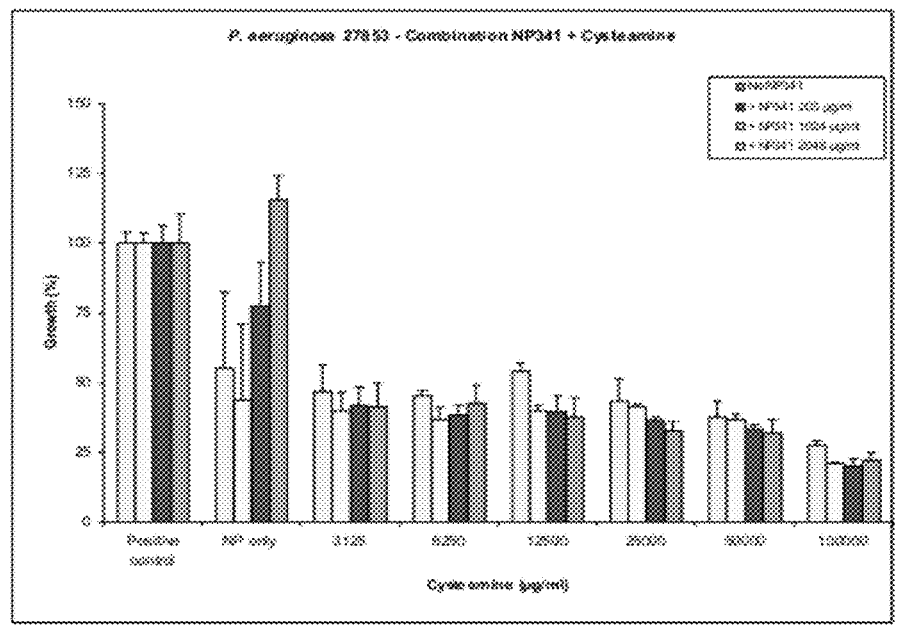
(b)
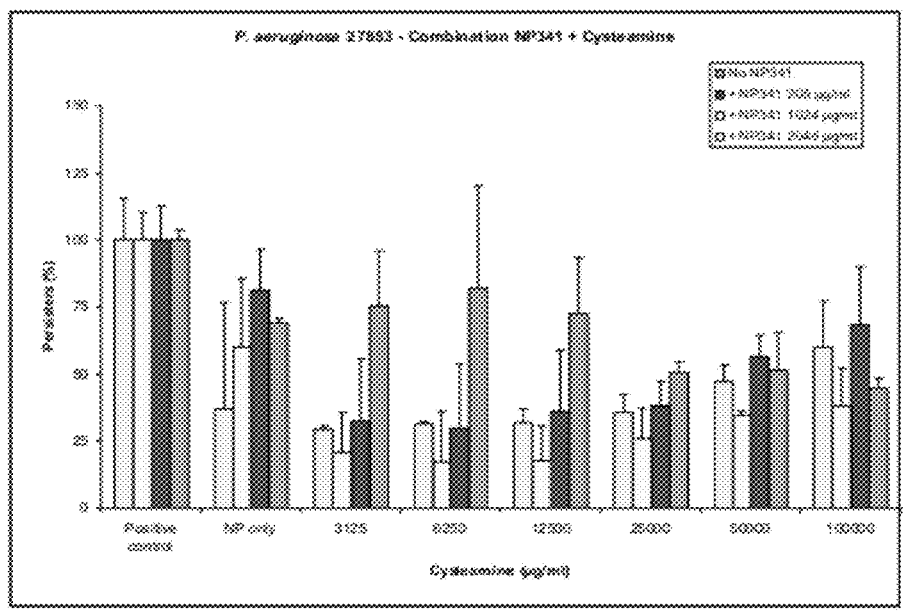

Fig 23a S. aureus 25923 24h-biofilm - untreated control
Fig 23b S. aureus 25923 24h-biofilm - NM001 2 mg/ml
Fig 23c S. aureus 25923 24h-biofilm - Colistin 0.2
Fig 23d S. aureus 25923 24h-biofilm - NP108 2

INHIBITION OF BIOFILM ORGANISMS

CROSS-REFERENCE TO RELATED APPLICATIONS

This present invention is a U.S. National Phase application of PCT Patent Application No. PCT/GB2010/000631, filed on Mar. 31, 2010 and claims priority to United Kingdom Patent Application No. GB 0905451.1 filed on Mar. 31, 2009, which claims priority to U.S. Provisional Patent Application No. U.S. 61/165,396, filed on Mar. 31, 2009, the disclosures of which are incorporated by reference in their entirety for all purposes.

FIELD OF THE INVENTION

The invention relates to products, compositions, methods and uses which are useful in relation to the prevention and treatment of biofilms.

BACKGROUND OF THE INVENTION

A microbial biofilm is a community of microbial cells embedded in an extracellular matrix of polymeric substances and adherent to a biological or a non-biotic surface. A range of microorganisms (bacteria, fungi, and/or protozoa, with associated bacteriophages and other viruses) can be found in these biofilms. Biofilms are ubiquitous in nature, are commonly found in a wide range of environments. Biofilms are being increasingly recognised by the scientific and medical community as being implicated in many infections, and especially their contribution to the recalcitrance of infection treatment.

Biofilms are etiologic agents for a number of disease states in mammals and are involved in 80% of infections in humans. Examples include skin and wound infections, middle-ear infections, gastrointestinal tract infections, peritoneal membrane infections, urogenital tract infections, oral soft tissue infections, formation of dental plaque, eye infections (including contact lens contamination), endocarditis, infections in cystic fibrosis, and infections of indwelling medical devices such as joint prostheses, dental implants, catheters and cardiac implants.

Planktonic microbes (i.e., microorganisms suspended or growing in a liquid medium) are typically used as models for antimicrobial susceptibility research as described by the Clinical and Laboratory Standards Institute (CLSI) and European Committee on Antimicrobial Susceptibility Testing (EUCAST). Microbes in biofilms are significantly more resistant to antimicrobial treatment than their planktonic counterparts. However, there is no standardized method for the study of antibiotic susceptibility of biofilm microbes.

Biofilm formation is not limited solely to the ability of microbes to attach to a surface. Microbes growing in a biofilm are able to interact more between each other than with the actual physical substratum on which the biofilm initially developed. For example, this phenomenon favours conjugative gene transfer, which occurs at a greater rate between cells in biofilms than between planktonic cells. This represents an increased opportunity for horizontal gene transfer between bacteria, and is important because this can facilitate the transfer of antibiotic resistance or virulence determinant genes from resistant to susceptible microbes. Bacteria can communicate with one another by a system known as quorum sensing, through which signalling molecules are released into the environment and their concentration can be detected by the surrounding microbes. Quorum sensing enables bacteria to co-ordinate their behaviour, thus enhancing their ability to survive. Responses to quorum sensing include adaptation to availability of nutrients, defense against other microorganisms which may compete for the same nutrients and the avoidance of toxic compounds potentially dangerous for the bacteria. It is very important for pathogenic bacteria during infection of a host (e.g. humans, other animals or plants) to co-ordinate their virulence in order to escape the immune response of the host in order to be able to establish a successful infection.

Biofilm formation plays a key role in many infectious diseases, such as cystic fibrosis and periodontitis, in bloodstream and urinary tract infections and as a consequence of the presence of indwelling medical devices. The suggested mechanisms by which biofilm-associated microorganisms elicit diseases in their host include the following: (i) delayed penetration of the antimicrobial agent through the biofilm matrix, (ii) detachment of cells or cell aggregates from indwelling medical device biofilms, (iii) production of endotoxins, (iv) resistance to the host immune system, (v) provision of a niche for the generation of resistant organisms through horizontal gene transfer of antimicrobial resistance &/or virulence determinant genes, and (vi) altered growth rate (.i.e. metabolic dormancy) (Donlan and Costerton, Clin Microbiol Rev 15: 167-193, 2002; Parsek and Singh, Annu Rev Microbiol 57: 677-701, 2003; Costerton J W, Resistance of biofilms to stress. In 'The biofilm primer'. (Springer Berlin Heidelberg). pp. 56-64.2007).

Recent experimental evidence has indicated the existence within biofilms of a small sub-population of specialized non-metabolising persister cells (dormant cells). It is thought that these cells may be responsible for the high resistance/tolerance of biofilm to antimicrobial agents. Multi-drug-tolerant persister cells are present in both planktonic and biofilm populations and it appears that yeasts and bacteria have evolved analogous strategies that assign the function of survival to this sub-population. The protection offered by the polymeric matrix allows persister cells to evade elimination and serve as a source for re-population. There is evidence that persisters may be largely responsible for the multi-drug tolerance of microbial biofilms (LaFleur et al., Antimicrob Agents Chemother. 50: 3839-46, 2006; Lewis, Nature Reviews Microbiology 5, 48-56 2007).

There remains a need for better therapies for preventing biofilm formation and treating conditions associated with microbial biofilms.

DESCRIPTION OF THE DRAWINGS

The invention will now be described by way of Examples only with reference to the following Figures in which:

FIG. 14: Antibacterial activity of NP339 and NM001 (cysteamine) combinations against (a) P. aeruginosa DSM 1128, (b) P. aeruginosa ATCC BAA-47, (c) P. aeruginosa DSM 1299 and (d) P. aeruginosa ATCC 27853 biofilm cells FIG. 15: Antibacterial activity of NP339 and NM001 (cysteamine) combinations against (a) P. aeruginosa DSM 1128 and (b) P. aeruginosa ATCC BAA-47 persister cells FIGS. 20 and 21: Activity of the mucolytic agents N-acetylcysteine (FIGS. 20(a) and 20(b)) and NM001 (cysteamine) (FIGS. 21(a) and 21(b)) alone and in combination with NP341 against P. aeruginosa 27853 planktonic cells

Figure 1:
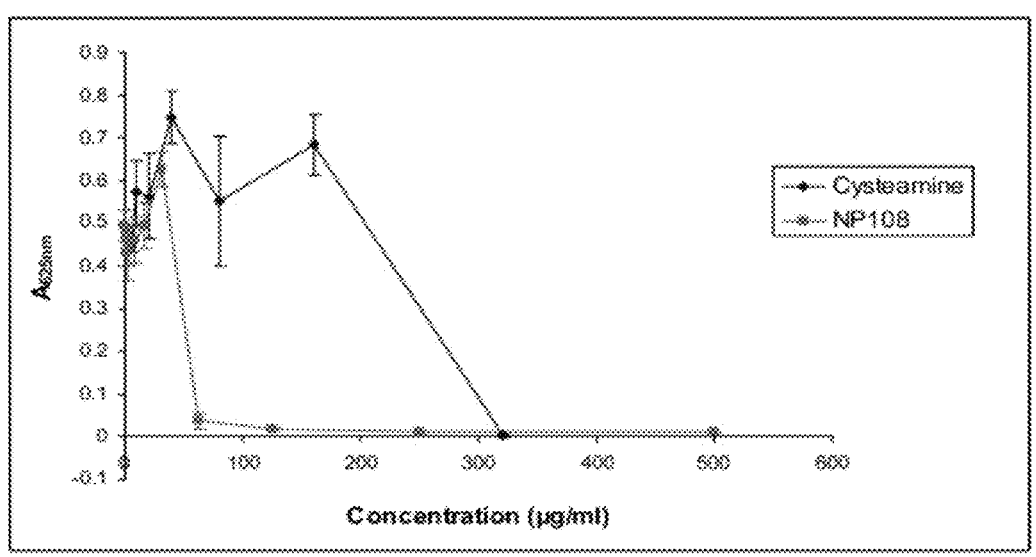
FIG. 1: Antibacterial activity of NP108 and NM001 (cysteamine) against *P. aeruginosa* ATCC BAA-47 planktonic cells

Table 2: Summary of the activity of the tested antimicrobial agents against S. epidermidis, S. aureus, and P. aeruginosa.

The present invention relates to a product comprising at least two antibiofilm agents wherein at least one of the antibiofilm agents is an antimicrobial peptide. The second antibiofilm agent is generally a dispersant or an anti-adhesive agent. There is also provided the use of the product in the treatment of a microbial infection.

TABLE 1

| | | Exp#1-2 | | | | | |
|---|---|---|---|---|---|---|---|
| | | MIC (µg/ml) at pH 7 | | | | | |
| NP | Sequence | S. epidermidis ATCC12228 | S. aureus ATCC25923 | S. aureus DSMZ11729 | P. aeruginosa DSMZ1128 | P. aeruginosa DSMZ1299 | P. aeruginosa ATCCBAA-47 |
| NP432 | RRRFRFFFRFRRR | <7.8 | 31.25 | 62.5 | 62.5 | 15.6 | 15.6 |
| NP438 | HHHFRFFFRFRRR | <7.8 | >500 | >500 | >500 | 500 | >500 |
| NP441 | HHPRRKPRRPKRHH | >500 | >500 | >500 | >500 | >500 | >500 |
| NP445 | KKFPWRLRLRYGRR | <7.8 | 500 | 500 | 62.5 | 31.25 | 31.25 |

TABLE 1-continued

Exp#1-2

| | | MIC (µg/ml) at pH 7 | | | | | |
|---|---|---|---|---|---|---|---|
| NP | Sequence | S. epidermidis ATCC12228 | S. aureus ATCC25923 | S. aureus DSMZ11729 | P. aeruginosa DSMZ1128 | P. aeruginosa DSMZ1299 | P. aeruginosa ATCCBAA-47 |
| NP449 | KKPRRKPRRPKRKK-cyst | 31.25 | 250 | 125 | 250 | 125 | 250 |
| NP451 | HHPRRKPRRPKRHH-cyst | 125 | 500 | 500 | >500 | >500 | >500 |
| NP457 | RRRRR-cyst | 31.25 | 125 | 125 | >500 | >500 | 250 |
| NP458 | RRRRRHH-cyst | 31.25 | 250 | 250 | 250 | 125 | 62.5 |

TABLE 2

| | MBC (µg/ml) following MIC at pH 7 | | | | | | Exp#3 | |
|---|---|---|---|---|---|---|---|---|
| NP | P. aeruginosa DSMZ1299 | S. epidermidis ATCC12228 | S. aureus ATCC25923 | S. aureus DSMZ11729 | P. aeruginosa DSMZ1128 | P. aeruginosa DSMZ1299 | P. aeruginosa ATCCBAA-47 | P. aeruginosa DSMZ1299 |
| NP432 | | 16 | 250 | 500 | 250 (2) | 32 (2) | 250 | |
| NP438 | | 125 | >500 | >500 | >500 | >500 | >500 | |
| NP441 | >500 | >500 | >500 | >500 | >500 | >500 | >500 | >500 |
| NP445 | | 62.5 | >500 | >500 | 250 | 125 | 250 | |
| NP449 | | 125 | >500 | 250 | 500 (2) | 250 (2) | >500 | |
| NP451 | >500 | 125 | >500 | >500 | >500 | >500 | >500 | >500 |
| NP457 | >500 | 125 (2) | 62.5 | 125 (2) | >500 | >500 | >500 | >500 |
| NP458 | | 500 | 125 | 250 | >500 | >500 | >500 | |

| | Exp#4 MIC (µg/ml) pH 5.5 | | Exp#3 MIC (µg/ml) pH 5.5, 320 mM NaCl | | Exp#4 MBC (µg/ml) at pH 5.5 | | MBC (µg/ml) pH 5.5, 320 mM NaCl | |
|---|---|---|---|---|---|---|---|---|
| NP | S. aureus 11729 | P. aeruginosa ATCCBAA-47 | S. aureus 11729 | P. aeruginosa ATCCBAA-47 | S. aureus 11729 | P. aeruginosa ATCCBAA-47 | S. aureus 11729 | P. aeruginosa ATCCBAA-47 |
| NP432 | >500 | 125 | >500 | 125 | >500 | 125 | >500 | >500 |
| NP438 | >500 | 125 | >500 | 62.5 | >500 | >500 | >500 | >500 |
| NP441 | >500 | >500 | >500 | >500 | >500 | >500 | >500 | >500 |
| NP445 | >500 | >500 | >500 | >500 | >500 | >500 | >500 | >500 |
| NP449 | >500 | >500 | >500 | >500 | >500 | >500 | >500 | >500 |
| NP451 | >500 | >500 | >500 | >500 | >500 | 250 | >500 | >500 |
| NP457 | >500 | >500 | >500 | >500 | >500 | >500 | >500 | >500 |
| NP458 | >500 | >500 | >500 | >500 | >500 | >500 | >500 | >500 |

DETAILED DESCRIPTION OF THE INVENTION

According to a first aspect of the present invention there is provided a product comprising at least two antibiofilm agents wherein at least one of the antibiofilm agents is an antimicrobial peptide. The other antibiofilm agent may be a dispersant or an anti-adhesive agent.

The term "antibiofilm agent" is used herein to describe an agent that is capable of destroying or inhibiting the growth of a microbial biofilm. The antibiofilm agent may be capable of disrupting the structure of the biofilm, for example the extracellular mucous matrix, or may be capable of destroying or inhibiting the growth of microbial cells within the biofilm.

The invention further provides a method of preventing biofilm formation in an environment comprising the step of administering to the environment an antimicrobial peptide. Advantageously the method comprises the step of administering to the environment a product according to the invention.

The invention further provides a method for treating a microbial infection, particularly a microbial biofilm, by prophylaxis or therapy, comprising the administration in a therapeutically effective amount of an antimicrobial peptide, for example a cationic peptide. Typically the method involves the sequential or combined administration in a therapeutically effective amount of:

a first antibiofilm agent; and a second antibiofilm agent different from the first one; wherein at least one of the first and second antibiofilm agents is an antimicrobial peptide for example a cationic peptide.

The above mentioned active agents may be administered as free or fixed combinations. Free combinations may be provided as combination packages containing all the active agents in free combinations. Fixed combinations are often tablets or capsules.

Included in the invention is the use in the manufacture of a medicament for the treatment of a microbial infection, particularly a microbial biofilm infection, by prophylaxis or therapy of the antimicrobial peptides, or combinations of active agents outlined above.

The products have the advantage that they demonstrate antibacterial activity against, inter alia, the persister cells present in the biofilms, which is an essential step towards the eradication of biofilms.

The agents of the invention may be administered in the form of pharmaceutically acceptable salts. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The invention thus includes pharmaceutically-acceptable salts of the disclosed compounds wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention therefore includes pharmaceutical products generally comprising at least:
 a first antibiofilm agent; and
 a second antibiofilm agent different from the first one wherein at least one of the first and second antibiofilm agents is an antimicrobial peptide for example a cationic peptide.
The First Antibiofilm Agent The first antibiofilm agent may be an antimicrobial peptide for example an antibacterial peptide. Preferably the first antibiofilm agent is an antimicrobial peptide, hereinafter referred to as "the first antimicrobial agent". The first antimicrobial agent may comprise amino acids according to the formula I:

$$((X)_l(Y)_m)_n \qquad (I)$$

wherein l and m are integers from 1 to 10, for example 1 to 5; n is an integer from 1 to 10; X and Y, which may be the same or different, are independently a hydrophobic or cationic amino acid.

Preferably the first antimicrobial agent comprises amino acids according to the formula (I) wherein X and Y are cationic amino acids.

The antimicrobial peptide may comprise from 2 to 200 amino acids, for example 3, 4, 5, 6, or 7 up to 100 amino acids, including 3, 4, 5, 6, or 7 up to 10, 15, 20, 25, 30, 35, 40, 45 or 50 amino acids. According to one embodiment, the antimicrobial peptide comprises 3 or 4 to 50 amino acids. Alternatively the peptide may comprise more than 27 amino acids, typically 27 to 300 amino acids, suitably 27 to 200 amino acids.

The peptide may comprise 100 to 200 amino acids, 20 to 100, 20 and 45 amino acids such as 20, 25, 30, 35, 40, 42 or 45 amino acids. The peptide may comprise between 3 and 15 amino acids, for example 5 to 15 amino acids.

As used herein, the term "hydrophobic" refers to an amino acid having a side chain that is uncharged at physiological pH, that is not polar and that is generally repelled by aqueous solution.

As used herein, the term "cationic" refers to amino acids having a net charge that is greater than or equal to 0. Generally the term "cationic" refers to amino acids having a net charge that is greater than zero.

Generally a hydrophobic amino residue has a hydrophobicity greater than or equal to −1.10 and a charge greater than or equal to 0.

Hydrophobic amino acids may include, leucine phenylalanine, proline, alanine, tryptophan, valine, isoleucine and methionine.

Preferably X and/or Y are cationic amino acids for example selected from the group consisting of histidine, arginine and lysine. Preferably still X and/or Y are arginine or lysine. X and/or Y may be selected from non-naturally occurring amino acids for example the cationic amino acid ornithine.

X and/or Y may be optical isomers of a cationic amino acid as defined herein for example D or L-amino acids. Moreover, X and/or Y may be alternating amino acids.

The amino acids may be naturally occurring or synthetic. The invention also includes known isomers (structural, stereo-, conformational & configurational) and structural analogues of the above amino acids, and those modified either naturally (e.g. post-translational modification) or chemically, including, but not exclusively, phosphorylation, glycosylation, sulfonylation and/or hydroxylation.

According to one embodiment the peptide may include one or more substitution of the cationic or hydrophobic amino acids X and Y. However, the peptide would predominantly comprise the cationic or hydrophobic amino acids X and Y. Typically the peptide may comprise 1 to 5 substitutions, suitably 1 to 3 substitutions, generally one substitution. The substitutions may be terminal or non-terminal.

The substitutions may consist of amino acids, or non-amino acids. The substitutions may be charged or uncharged. Typically one or more of the substitutions are uncharged amino acids. Alternatively or additionally one or more of the substitutions may be non-amino acids such as cysteamine.

Preferably X and Y are the same and are lysine or arginine.

According to one embodiment, the peptide comprises predominantly arginine amino acids which may be substituted with one or more amino acids which are not arginine.

Generally the peptide comprises 7 to 20 arginine amino acids, optionally substituted with 1 to 5 non-arginine amino acids, typically 3 to 5 non-arginine substitutions.

Alternatively the peptide may comprise 7 to 20 lysine amino acids, optionally substituted with 1 to 5 non-lysine amino acids, typically 3 to 5 non-lysine substitutions.

According to a further embodiment, the peptide may comprise 27 to 300 lysine amino acids, generally 27 to 200 lysine amino acids. Typically the peptide comprises no non-terminal substitutions with non-lysine amino acids.

In the peptide of formula (I) l and m may be 1, 2, 3, 4, 5, 6, 7, 8, 9 or 10 and n may be 1, 2, 3, 4, 5, 6, 7, 8, 9 or 10.

In the peptide of formula (I) l may be 1, n may be l and m may be between 4 and 9, for example, m may be 3, 4, 5, 6, 7, 8 or 9.

In the peptide of formula (I) l, n and/or m may be between 1 and 5, for example, 1, 2, 3, 4 or 5.

In the peptide of formula (I) l and m may be an integer between 0 and 7 and n may be an integer between 1 and 10.

In the peptide of formula (I) l and m may be 0, 1 or 2 and n may be an integer between 1 and 10.

In the peptide of formula (I) X and Y may be the same, l may be 0, m may be 1 and n may be 3, 4, 5, 6, 7, 8, 9 or 10.

In the peptide of formula (I) X and Y may be the same, l and m may be 1 and n may be 2, 3, 4 or 5.

In the peptide of formula (I) X and Y may be the same, l may be 1, m may be 2 and n may be 1, 2, 3 or 4.

In the peptide of formula (I) X and Y may be the same, l and m may be 2 and n may be 1, 2, 3 or 4.

Preferably the first antimicrobial agent comprises a peptide sequence selected from the group consisting of polylysine and polyarginine.

In one embodiment, the first antimicrobial agent comprises a polylysine.

In an alternative embodiment, the first antimicrobial agent comprises polyarginine.

According to a further aspect of the present invention there is provided the use of the first antimicrobial agent in the treatment of prevention of a biofilm.

Typically the first antimicrobial agent is in the form of the product of the invention as described below.

The Second Antibiofilm Agent

The second antibiofilm agent may be any agent which inhibits biofilm formation. By way of example, the second antibiofilm agent may inhibit bacterial adhesion, hydrophobicity or slime production. The second antibiofilm agent may be selected from a dispersant and an anti-adhesive agent.

According to one embodiment of the present invention the second antibiofilm agent is not a peptide.

The term "dispersant" is intended to include any agent capable of dispersing the particles of a biofilm. In particular, the dispersant may promote the dispersion of slime produced by microbes such as bacteria, mucous which forms part of the biofilm for example mucous produced by the cells to which the biofilm microbes adheres, and biofilm microbes such as bacteria.

The dispersant may be a mucolytic agent. The mucolytic agent may be an enzyme for example a DNase, alginase, protease or carbohydrase. Alternatively the mucolytic agent may be a small molecule for example an amine such as an aminothiol or an acid such as ethylenediaminetetraacetic acid (EDTA). The amine may be selected from acetylcysteine and cysteamine.

The term "anti-adhesive agent" is intended to include any agent capable of inhibiting adhesion between cells, proteins and organisms e.g. microbes thereby preventing biofilm formation or promoting biofilm self-destruction. In particular, the anti-adhesive agent may prevent the adhesion to a surface or substrate of all cell types encountered in microbial biofilms in particular free living microbes i.e. planktonic cells. Anti-adhesive agents may include, but are not limited to, hyaluronan, heparin or Carbopol 934.

The second antibiofilm agent may be an antibacterial agent. The antibacterial agent may be a mucolytic agent for example a mucolytic agent having both mucolytic and antibacterial activity. Preferably the antibacterial agent is cysteamine.

The Products of the Invention

The product of the present invention may comprise an antimicrobial peptide.

A preferred product comprises an antimicrobial peptide and a mucolytic agent.

The ratio of the first antibiofilm agent to the second antibiofilm agent in the products of the invention may be from 1:10 to 10:1; generally at least 2:1 for example at least 3:1 or 4:1. According to one embodiment, the ratio of first antibiofilm agent to the second antibiofilm agent is approximately 1:1. Preferably the first antibiofilm agent is a cationic peptide and the second antibiofilm agent is a mucolytic agent and the ratio of cationic peptide:mucolytic agent ranges from 2:1 up to 4:1. According to a further embodiment the ratio may be approximately 1:1.

The active agents may be administered simultaneously, sequentially or separately. The active agents may be provided as a combination package. The combination package may contain the product of the invention together with instructions for simultaneous, separate or sequential administration of each of the active agents. For sequential administration, the active agents can be administered in any order.

The active agents of the product of the invention may be provided as pharmaceutical compositions additionally containing one or more pharmaceutically acceptable diluents, excipients and/or carriers. This applies to both fixed and free combinations.

The active agents of the present invention may be administered by any suitable route known to those skilled in the art, preferably in the form of a pharmaceutical composition adapted to such a route, and in a dose effective for the treatment intended. The active compounds and composition may, for example, be administered parenterally, orally, intranasal, intrabronchial, enterally, transdermally, sublingually, rectally, vaginally, ocularly, or topically. Both local and systemic administration is contemplated.

For the purposes of parenteral administration ("parenteral" as used herein, refers to modes of administration which include intravenous, intramuscular, enteral, intraperitoneal, intrasternal, subcutaneous and intraarticular injection and infusion of which intravenous (including continuous intravenous administration) is most preferred) solutions in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

The products of the invention can also be administered intranasally or by inhalation and are conveniently delivered in the form of a dry powder inhaler or an aerosol spray presentation from a pressurised container, pump, spray, atomiser, nebuliser, with or without the use of a suitable propellant.

Alternatively the products of the invention can be administered in the form of a suppository or pessary, or they may be applied topically in the form of a gel, hydrogel, lotion, solution, cream, ointment or powder. The products of the invention may be dermally or transdermally administered, for example, by use of a skin patch, depot or subcutaneous injection. They may also be administered by pulmonary or rectal routes.

For oral administration, the pharmaceutical composition may be in the form of; for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose; mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient may also be administered by injection as a composition wherein, for example, saline, dextrose or water may be used as a suitable carrier.

The products of the invention may also find application as/in an oral formulation wherein the product is formulated in a carrier, for example selected from films, tapes, gels, microspheres, lozenges, chewing gum, dentrifices and mouthwash.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

The products of the invention are preferably administered to the respiratory tract. Thus, the present invention also provides aerosol pharmaceutical formulations comprising a product of the invention. Also provided is a nebuliser or inhaler containing a product of the invention.

Additionally, the products of the invention may be suited to formulation as sustained release dosage forms and the like. The formulations can be so constituted that they release the active agents, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g. stents, catheters, peritoneal dialysis tubing, draining devices and the like.

The products of the invention may include synergistically effective amounts of each active agent defined herein. The invention therefore includes products comprising a synergistically effective amount of (i) a first antibiofilm agent, (ii) a second antibiofilm agent which is different from the first antibiofilm agent and is typically an antimicrobial peptide. The product may be for use in the manufacture of a medicament, for simultaneous, separate or sequential administration said agents in the treatment of a microbial infection for example a biofilm infection. "Synergistically", as used herein, may describe the action of the two or more agents of the product of the invention working together to produce an effect greater than the expected combined effect of the agents used separately.

In a further aspect of the invention there is provided a substrate to which a product of the invention is applied or attached. Preferably, the substrate is suitable for application to wounds or delivery to wound sites. Preferably, the substrate allows for the transfer of the active agents of the product of the invention from the substrate to a wound bed to achieve their antibiofilm effect. The substrate may be a dressing, for example, wound dressing. The dressing may comprise a fabric material or it may be a collagen-like material. The substrate may be in any suitable form for application to a wound, typically the substrate may be in the form of a hydrogel, colloid, ointment, cream, gel, foam or spray.

The products of the invention may also find application as/in a disinfectant or biocide. In this context, the peptide or pharmaceutical compositions of the invention may be applied, either alone or in combination with other disinfecting agents, to a surface to be treated. As used herein a "surface to be treated" may be a substrate as defined herein and may include medical devices and indwelling devices, e.g. stents, catheters, peritoneal dialysis tubing, draining devices, joint prostheses, dental implants and the like.

Methods and Use

The invention provides a method of preventing biofilm formation in an environment comprising the step of administering to the environment a product according to the invention. The method may be in vivo or ex vivo.

According to one embodiment, the method comprises the step of administering an antimicrobial peptide.

Advantageously the method comprises the step of administering a first antibiofilm agent; and a second antibiofilm agent different from the first one wherein at least one of the first and second antibiofilm agents is an antimicrobial peptide for example a cationic peptide.

The environment may comprise any biofilm forming microorganism selected from bacteria, fungi, yeast, viruses and protozoa.

Typically the microorganism is a bacterium for example a Gram-positive or Gram-negative bacterium. A bacterial pathogen may be derived from a bacterial species selected from the group consisting of: *Staphylococcus* spp., e.g. *Staphylococcus aureus, Staphylococcus epidermidis; Enterococcus* spp., e.g. *Enterococcus faecalis; Streptococcus pyogenes; Listeria* spp.; *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptococcus* Group A or B, *Streptoccocus pneumoniae; Helicobacter* spp., e.g. *Helicobacter pylori; Neisseria* spp., e.g. *Neisseria gonorrhea, Neisseria meningitidis; Borrelia* burgdorferi; Shigella spp., e.g. Shigella flexneri; Escherichia coli; Haemophilus spp., e.g. Haemophilus influenzae; Chlamydia spp., e.g. Chlamydia trachomatis, Chlamydia pneumoniae, Chlamydia psittaci; Francisella fularensis; Bacillus spp., e.g. Bacillus anthracis; Clostridia spp., e.g. Clostridium botulinum; Yersinia spp., e.g. Yersinia pestis; Treponema spp.; Burkholderia spp.; e.g. Burkholderia mallei and B pseudomallei.

In particular the bacterium may include Pseudomonas spp., for example Pseudomonas aeruginosa; Staphylococcus spp., for example Staphylococcus aureus and Staphylococcus epidermidis; Haemophilus spp., for example Haemophilus influenza; Burkholderia spp., for example Burkholderia cepacia; Streptococcus spp., Propionibacterium spp., for example Propionibacterium acnes. Preferably the bacterium is selected from Pseudomonas spp., for example Pseudomonas aeruginosa and Staphylococcus spp., for example Staphylococcus aureus and Staphylococcus epidermidis.

A viral pathogen may be derived from a virus selected from the group consisting of: Human Immunodeficiency Virus (HTV1 & 2); Human T Cell Leukaemia Virus (HTLV 1 & 2); Ebola virus; human papilloma virus (e.g. HPV-2, HPV-5, HPV-8 HPV-16, HPV-18, HPV-31, HPV-33, HPV-52, HPV-54 and HPV-56); papovavirus; rhinovirus; poliovirus; herpesvirus; adenovirus; Epstein Barr virus; influenza virus, hepatitis B and C viruses, Variola virus, rotavirus or SARS coronavirus.

A parasitic pathogen may be derived from a parasitic pathogen selected from the group consisting of Trypanosoma spp. (Trypanosoma cruzi, Trypansosoma brucei), Leishmania spp., Giardia spp., Trichomonas spp., Entamoeba spp., Naegleria spp., Acanthamoeba spp., Schistosoma spp., Plasmodium spp., Crytosporidiwn spp., Isospora spp., Balantidium spp., Loa Loa, Ascaris lumbricoides, Dirofilaria immitis, Toxoplasma ssp., e.g Toxoplasma gondii. A fungal pathogen may be derived from a fungal pathogen which is of the genus Candida spp., (e.g. C. albicans), Epidermophyton spp., Exophiala spp., Microsporiim spp., Trichophyton spp., (e.g T. rubrum and T. interdigitale), Tinea spp., Aspergillus spp., Blastomyces spp., Blastoschizomyces spp., Coccidioides spp., Cryptococcus spp., Histoplasma spp., Paracoccidiomyces spp., Sporotrix spp., Absidia spp., Cladophialophora spp., Fonsecaea spp., Phialophora spp., Lacazia spp., Arthrographis spp., Acremonium spp., Actinomadura spp., Apophysomyces spp., Emmonsia spp., Basidiobolus spp., Beauveria spp., Chrysosporium spp., Conidiobolus spp., Cunninghamella spp., Fusarium spp., Geotrichum spp., Graphium spp., Leptosphaeria spp., Malassezia spp., Mucor spp., Neotestudina spp., Nocardia spp., Nocardiopsis spp., Paecilomyces spp., Phoma spp., Piedraia spp., Pneumocystis spp., Pseudallescheria spp., Pyrenochaeta spp., Rhizomucor spp., Rhizopus spp., Rhodotorula spp., Saccharomyces spp., Scedosporium spp., Scopulariopsis spp., Sporobolomyces spp., Syncephalastrum spp., Trichoderma spp., Trichosporon spp., Ulocladium spp., Ustilago spp., Verticillium spp., Wangiella spp.

According to a further embodiment the microorganism may be a fungi, in particular Candida.

The method of the invention may be used to minimise and, preferably, prevent the formation of biofilms in a variety of environments including, but not limited to, household, workplace, laboratory, industrial environment, aquatic environment (e.g. pipeline systems), medical devices including indwelling devices such as defined herein, dental devices or dental implants, animal body for example human body.

The method of the invention may thus be used in the mouth to prevent the formation of plaque or caries on a human tooth or dental implant for example a denture.

The method of the invention may be used to prevent or restrict the formation of a biofilm in the human body especially in the treatment of microbial infections. Conditions associated with biofilm infections may include topical infections, oral infections and systemic infections. Topical infections may include wounds, ulcers and lesions for example, cutaneous wounds such cuts or burns, and conditions associated therewith.

Oral infections may include gingivitis, periodontitis and mucositis.

Systemic infections may include cystic fibrosis and other conditions associated with mucosal infections, for example, gastrointestinal, urogenital or respiratory infections.

Another aspect of the invention resides in methods of treating, preventing or delaying the progression of a disease or condition associated with the presence of a microbial biofilm infection in a mammal, especially a human, by administering a therapeutically effective amount of a product of the invention to the mammal.

By an "effective" amount or "therapeutically effective amount" is meant an amount of one or more active substances which, within the scope of sound medical judgment, is sufficient to provide a desired effect without excessive toxicity, irritation, allergic response, or other problem or complication, commensurate with a reasonable benefit/risk ratio.

According to one aspect of the present invention the method comprises the step of administering an antimicrobial peptide.

Advantageously the method comprises the step of administering a first antibiofilm agent; and a second antibiofilm agent different from the first one wherein at least one of the first and second antibiofilm agents is an antimicrobial peptide for example a cationic peptide.

The invention further provides the use of a product of the invention in the manufacture of a medicament for the treatment of a microbial infection, particularly a microbial biofilm infection, by prophylaxis or therapy of the combinations of active agents outlined above.

Additionally the present invention provides the use of the antimicrobial peptide described above in the manufacture of a medicament for the treatment of a microbial infection, particularly a microbial biofilm infection, by prophylaxis or therapy.

Thus the product of the invention may be useful in the prevention of, delay of progression of, or treatment of a disease or condition selected from the group consisting of skin and wound infections, middle-ear infections, gastrointestinal tract infections, peritoneal membrane infections, urogenital tract infections, oral soft tissue infections, formation of dental plaque, eye infections (including contact lense contamination), endocarditis, infections in cystic fibrosis, and infections of indwelling medical devices such as described herein.

The invention also includes methods of treatment in which a product of the invention is administered to a mammal together with one or more other antibacterial agents for example an antibiotic.

The inventors have surprisingly found that certain dispersants, in particular mucolytic agents, inhibit the growth of biofilm persister cells. Thus the invention also includes a method of treating/preventing biofilm formation in an environment comprising administering to said environment a mucolytic agent, for example cysteamine. The mucolytic agent may be administered alone or in combination with another antimicrobial agent for example an antimicrobial peptide.

The invention also provides a method for treating a microbial infection, particularly a microbial biofilm, by prophylaxis or therapy, comprising the administration in a therapeutically effective amount of a dispersant, in particular a mucolytic agent, for example cysteamine.

The invention further provides the use of a dispersant, in particular a mucolytic agent, for example cysteamine, in the manufacture of a medicament for the treatment of a microbial infection, particularly a microbial biofilm infection.

The active agents mentioned in this specification can exist in different forms, such as free acids, free bases, esters and other prodrugs, salts and tautomers, for example, and the invention includes all variant forms of the agents.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Generally the term "approximately" is intended to encompass a range of 10% or less of any numerical value to which it is applied.

Further aspects and embodiments of the invention are set forth in the following description and claims.

EXAMPLES

Activity of Antimicrobial Agents Against Bacterial Biofilms

1. Materials and Methods
1.1 Bacterial strains

*Pseudomonas aeruginosa* ATCC27853, *P. aeruginosa* BAA-47 (PAO1), *P. aeruginosa* DSM1128, *P. aeruginosa* DSM1299 and *S. epidermidis* ATCC35984, *S. epidermidis* ATCC12228 *Staphylococcus aureus* 25923 and methicilin-resistant *Staphylococcus aureus* DSM 11729 (MRSA) (DSMZ, Braunschweig, Germany) were used in this study. Four *P. aeruginosa* clinical isolates (NH57388A-D, Hoffmann et al., 2005, 2007) were obtained and used for antimicrobial susceptibility testing.

1.2 Preparation of Antimicrobial Compounds

The antimicrobial agents tested in this study were the cationic peptide NP108, which corresponds to a 10-20 kDa poly-L-lysine, hydrobromide and cysteamine (NM001). Both agents were obtained from Sigma-Aldrich (Gillingham, UK) and stock solutions were prepared at 20 mg/ml in 14-18 MΩ·cm pure water (Purite HP40 water purification system, Oxon, UK). Once dissolved, the preparations were filter-sterilized using 0.22 μm filters (Millipore, Watford, England) and stored at −20° C.

The following NovaBiotics antimicrobial peptides were also investigated

```
NP339  dRdRdRdRdRdRdRdRdRdRdRdR
NP340  Ac-dRdRdRdRdRdRdRdRdRdRdRdR-CONH
NP341  dRdRdRdRdRdRdRdRdRdRdRdR-C ONH
NP352  RRRRRRRRRRRRRRR
NP432  RRRFRFFFRFRRR
NP438  HHHFRFFFRFRRR
NP441  HHPRRKPRRPKRRHH
NP445  KKFPWRLRLRYGRR
NP449  KKPRRKPRRPKRKK-cysteamine
NP451  HHPRRKPRRPKRHH-cysteamine
NP457  RRRRR-cysteamine
NP458  RRRRRHH-cysteamine
```

NovaBiotics antimicrobial peptides were synthesized by NeoMPS (Strasbourg, France) using Fmoc synthesis and were at least 95% pure.

1.3 Preparation of the Bacterial Inoculum

The bacterial inoculum was established by the dilution method from actively-growing cultures in Mueller-Hinton broth, standardized with 0.5 McFarland turbidity standard as described in the CLSI method M26-A.

1.4 Determination of the Minimum Inhibitory Concentration (MIC)

To determine the prevention of biofilm formation, both the bacterial inoculum and the antimicrobial agents were added simultaneously to the plates. The plates were incubated at 37° C. for 24 h and the optical density was read at 625 nm on a microtitre plate reader (BioTek Powerwave XS, Winooski, USA). The MIC was obtained as the lowest concentration of antimicrobial showing total inhibition of bacterial growth.

1.5 Determination of the Fractional Inhibitory Concentration (FIC)

The FIC corresponds to an interaction coefficient indicating whether the combination of antimicrobial agents is synergistic, additive, antagonist or neutral. The FIC is determined by comparing the activity of an agent in combination (MIC of agent A+agent B) with the activity of the agent alone (MIC of agent A or agent B) as follow (Singh et al., 2000):

$$FIC = MIC_{A[combination]}/MIC_{A[alone]} + MIC_{B[combination]}/MIC_{B[alone]}$$

Additive combinations of two antimicrobial agents are indicated by a FIC index of 1, whereas a FIC index <1 indicates synergistic combinations. Neutral combinations would give a FIC between 1 and 4, a FIC index higher than 4 indicates antagonist effects between the two antimicrobial agents.

The FIC was also calculated to assess the interaction of two antimicrobial agents in combination against bacterial biofilms. The same formulae applied, using MBEC instead of MIC.

1.6 Determination of the Minimum-Biofilm Eradication Concentration (MBEC)

A total volume of 100 μl bacterial inoculum in Mueller-Hinton was added to each well of 96-well plates (challenge plates) and the plates were incubated at 37° C. for 24 h on a gyrorotary shaking platform (Grant-bio PS-3D, Shepreth, England) at 24 rpm to allow for biofilm formation.

The challenge plates were then rinsed once with sterile PBS (1×) and two-fold serial dilutions of antimicrobial agents in Mueller-Hinton were added to the challenge plates. The challenge plates were incubated at 37° C. for 24 h on a gyrorotary shaking platform (Grant-bio PS-3D, Shepreth, England) at 24 rpm.

The supernatants from each of the challenge plates were transferred into fresh plates and the optical density was measured at 625 nm on a microtitre plate reader (BioTek Powerwave XS, Winooski, USA). The MBEC was obtained by the lowest concentration of antimicrobial showing no bacterial growth.

1.7 Estimation of the Persister Cells in the Biofilms

Following transfer of the supernatant from the challenge plates, the biofilms were rinsed once with sterile PBS (1×) and 100 µl of BacLight live/dead fluorescent staining solution (Invitrogen, Paisley, UK) containing 4 µM SYTO9 and 20 µM propidium iodide (PI) in sterile PBS (1×) were added to the wells of the challenge plates. The plates were incubated at room temperature in the dark for 15 min and the fluorescence was read at 485(ex)/528(em) and 485(ex)/645(em) for SYTO9 and PI fluorescence, respectively on a fluorescence microtitre plate reader (BioTek Synergy HT, Winooski, USA) with the sensitivity set at 50 and bottom optics position was selected. Direct observation of the biofilms with an Axiovert 40 fluorescence microscope (Zeiss, Gottingen, Germany) allowed identifying the presence of live and dead bacteria and pictures of the biofilms were taken at 100 to 400-fold magnification.

The relative viability of persister cells was determined by the live/dead fluorescence measurements ratio and microscopic observations were used to confirm the presence or absence of live cells.

2. Results 2.1 Prevention of Biofilm Formation

In order to assess for the prevention of biofilm formation by both Gram-positive and Gram-negative bacteria, the bacterial inoculum and antimicrobial agents were added simultaneously in the plates. The range of concentrations of antimicrobial agents was 0-500 µg/ml NP108 and 0-320 µg/ml cysteamine against the Gram-negative bacteria P. aeruginosa ATCC BAA-47 and 0-1000 µg/ml NP108 and 0-320 µg/ml cysteamine against the Gram-positive MRSA.

2.1.1 Activity Against P. aeruginosa ATCC BAA-47

The MIC of NP108 was 62.5 µg/ml and 320 µg/ml for cysteamine. NP108 was bactericidal at 250 µg/ml whereas cysteamine was not bactericidal at up to 320 µg/ml (data not shown).

In the presence of 160 µg/ml cysteamine the MIC of NP108 was reduced to 31.25 µg/ml. When the concentration of cysteamine was doubled (ie. 320 µg/ml) no growth was observed regardless of the concentration of NP108.

Determination of the FIC for this combination indicates that the antimicrobial agents have additive effects (FIC=1). Moreover, bactericidal activity was obtained in the presence of 125 µg/ml NP108 and 320 µg/ml cysteamine (data not shown), which confirms the additive effect of these agents.

2.1.2 Activity Against S. aureus DSM 11729

The MIC of NP108 was 125 µg/ml and more than 320 µg/ml for cysteamine. NP108 was bactericidal at 125 µg/ml whereas cysteamine was not bactericidal at up to 320 µg/ml (data not shown).

Increasing concentrations of cysteamine showed a higher inhibition of growth for any given concentration of NP108. In the presence of 40 µg/ml cysteamine the MIC of NP108 was reduced to 31.25 µg/ml and down to 15.625 µg/ml when 320 µg/ml cysteamine were added.

Determination of the FIC for this combination indicates that the antimicrobial agents have at least additive effects (FIC<1). Moreover, bactericidal activity was obtained in the presence of 31.25 µg/ml NP108 and ≥160 µg/ml cysteamine as well as 62.5 µg/ml NP108 and ≥80 µg/ml cysteamine (data not shown), which confirms the additive effect of these agents.

Appendix 1 shows the time course activity of the short linear arginine peptides (NP339, NP340, NP341 and NP352) against S. aureus DSM 11729 planktonic cells.

Appendix 2 provides a summary of the activity of NP108, cysteamine, both compounds in combination as well as the activity of NP339 and NP341 against S. aureus DSM 11729 and P. aeruginosa BAA-47 planktonic cells.

2.2 Destruction of Formed Biofilms

The assessment of the activity of NP108 and cysteamine against bacterial biofilms was carried out with 24 h-old biofilms and the activity of both compounds in combination was also determined. The activity of the antimicrobial agents against bacterial biofilms was determined by their activity against the biofilm cells and against the persister cells.

2.2.1 Activity of NP339 Against Bacterial Biofilms

Figure 5:
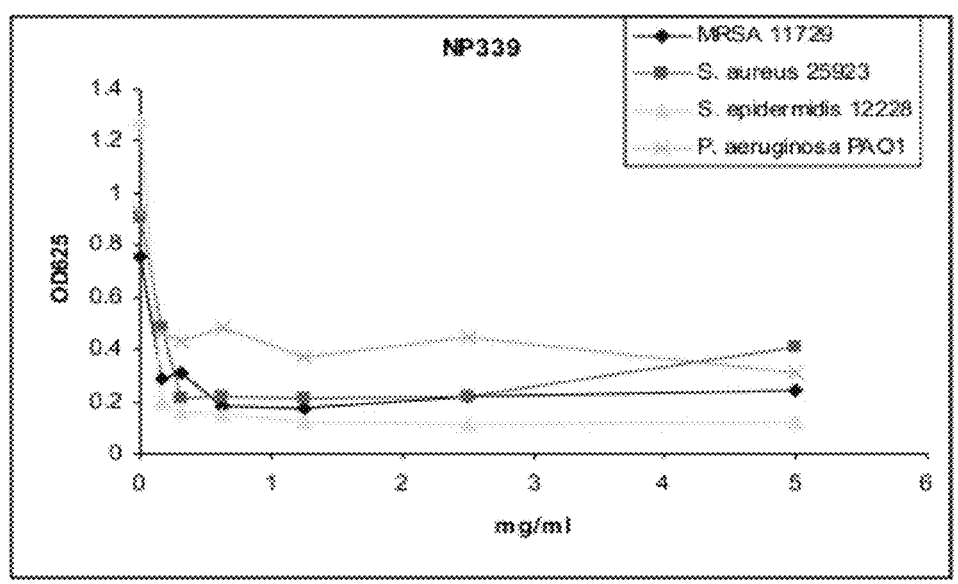
FIG. 5: Activity of NP339 against biofilm cells of Gram-positive and Gram-negative bacteria

FIG. 5 shows the high activity of NP339 against biofilms of 3 Staphylococcus species, resulting in MBEC of 156 to 625 µg/ml. The increase in optical density at the highest dose of NP339 against S. aureus 25923 is likely to be an artifact due to the complex and heterogeneous nature of microbial biofilms. In contrast NP339 reduced the growth P. aeruginosa BAA-47 (PAO1), but even the highest dose tested (i.e. 5 mg/ml) was not sufficient to inhibit 100% of the biofilm cells.

Figure 6:
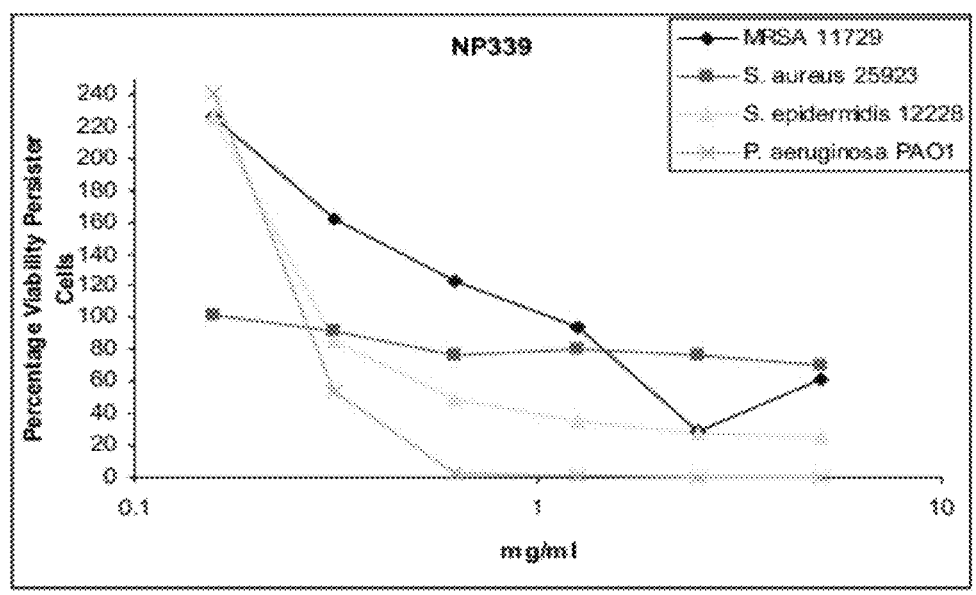
FIG. 6: Activity of NP339 against persister cells of Gram-positive and Gram-negative bacteria
Figure 7:
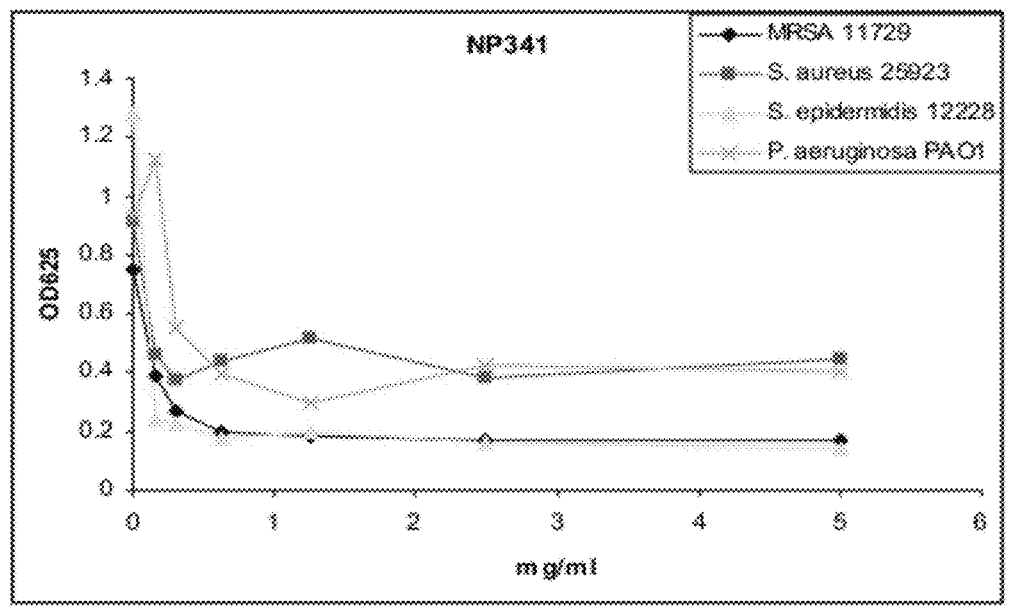
FIG. 7: Activity of NP341 against biofilm cells of Gram-positive and Gram-negative bacteria
Figure 8:
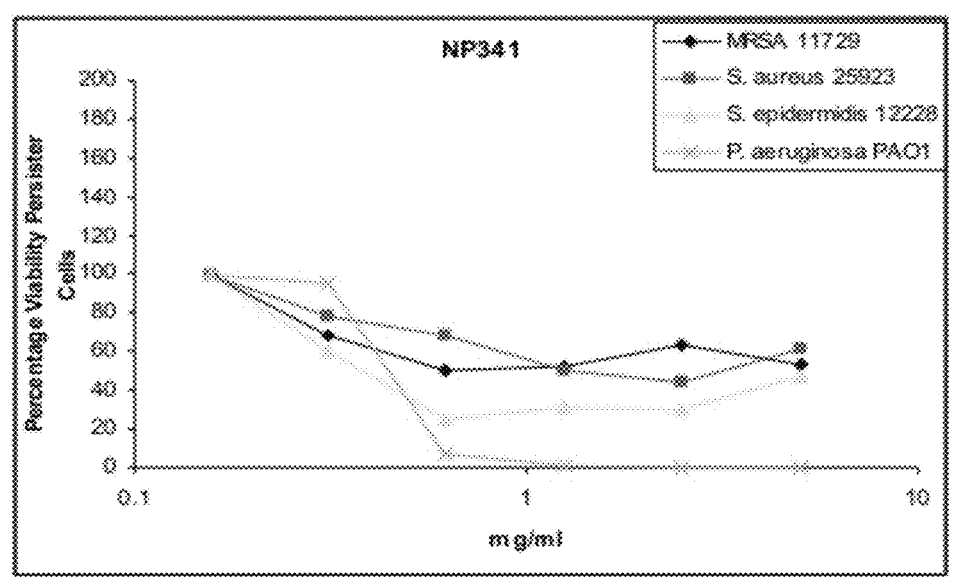
FIG. 8: Activity of NP341 against persister cells of Gram-positive and Gram-negative bacteria

FIG. 6 provides evidence that NP339 is active against persister cells. In contrast to the activity of NP339 against the biofilm cells of the 4 strains tested, it was less active against the persister cells of Staphylococcus species than those of P. aeruginosa BAA-47 (PAO1). NP339 was able to inhibit the viability of P. aeruginosa BAA-47 (PAO1) persister cells at 625 µg/ml.

2.2.2 Activity of NP341 Against Bacterial Biofilms

Similarly to NP339 (FIG. 5), NP341 showed significant reduction in biofilm cells viability. The MBEC for MRSA 11729 and S. epidermidis 12228 was 625 µg/ml. NP341 reduced the viability of biofilm cells of MRSA 11729 and P. aeruginosa BAA-47 (PAO1) by a 2 to 3-fold factor.

As seen with NP339, the viability of P. aeruginosa persister cells was totally inhibited at 625 µg/ml NP341. The viability of the persister cells of the 3 Staphylococcus species was decreased by 25 to 50%.

2.2.3 Activity of Cysteamine Against Bacterial Biofilms

Figure 9:
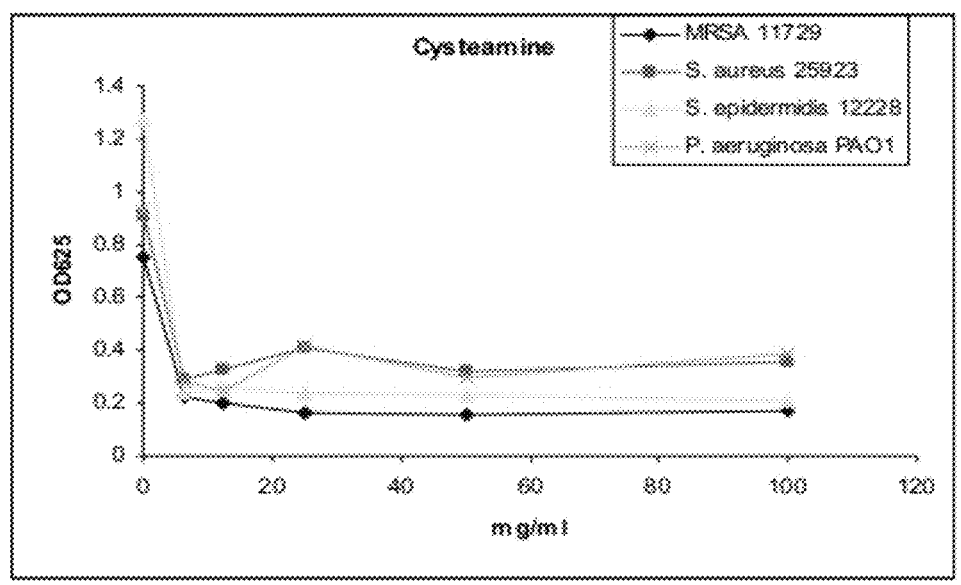
FIG. 9: Activity of NM001 (cysteamine) against biofilm cells of Gram-positive and Gram-negative bacteria

FIG. 9 provides evidence that cysteamine has antimicrobial activity against biofilm cells of the Gram-positive and Gram-negative bacteria tested.

Figure 10:
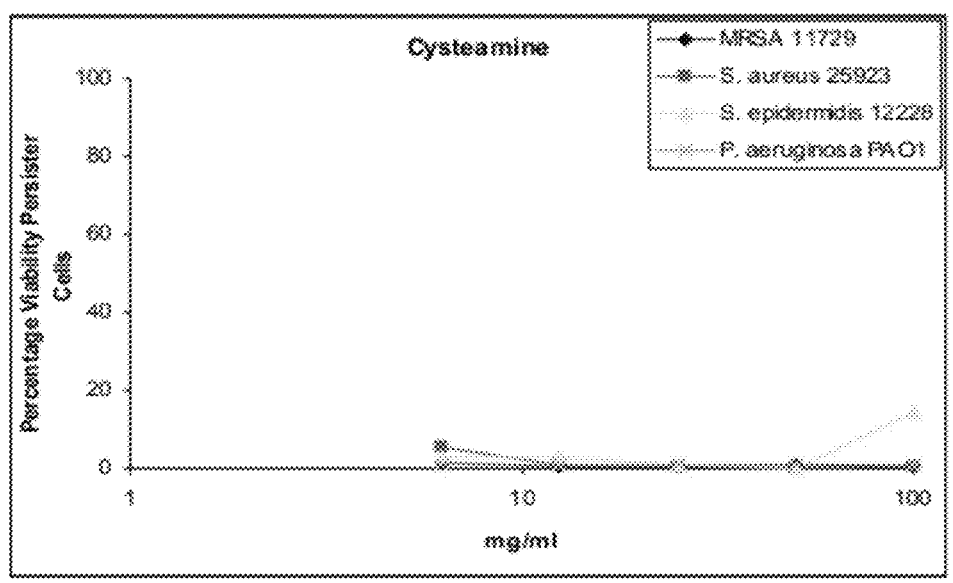
FIG. 10: Activity of NM001 (cysteamine) against persister cells of Gram-positive and Gram-negative bacteria

FIG. 10 shows the activity of cysteamine against persister cells of the Gram-negative and Gram-positive bacteria tested.

The results presented here show the antimicrobial activity of the linear short cationic peptides NP339 and NP341 against biofilms of Gram-positive and Gram-negative bacteria. These compounds appear more effective against the biofilm cells of Gram-positive bacteria than Gram-negative bacteria, whereas it is the opposite against persister cells. Cysteamine showed activity against biofilm cells at high concentrations, however, it suppressed the viability of both Gram-positive and Gram-negative persister cells at the lowest concentration tested (i.e. 6.25 mg/ml).

2.2.4 Activity of NP108 and Cysteamine in Combination Against P. aeruginosa ATCC BAA-47

The combination of these two antimicrobial agents showed complete inhibition of bacterial growth in the presence of 250 µg/ml NP108 and 62.5 to 500 µg/ml cysteamine. The addition of 31.25 µg/ml cysteamine to 500 µg/ml NP108 had a similar effect, whereas 31.25 µg/ml cysteamine plus 250 µg/ml NP108 showed only partial inhibition of bacterial growth.

Figure 2:
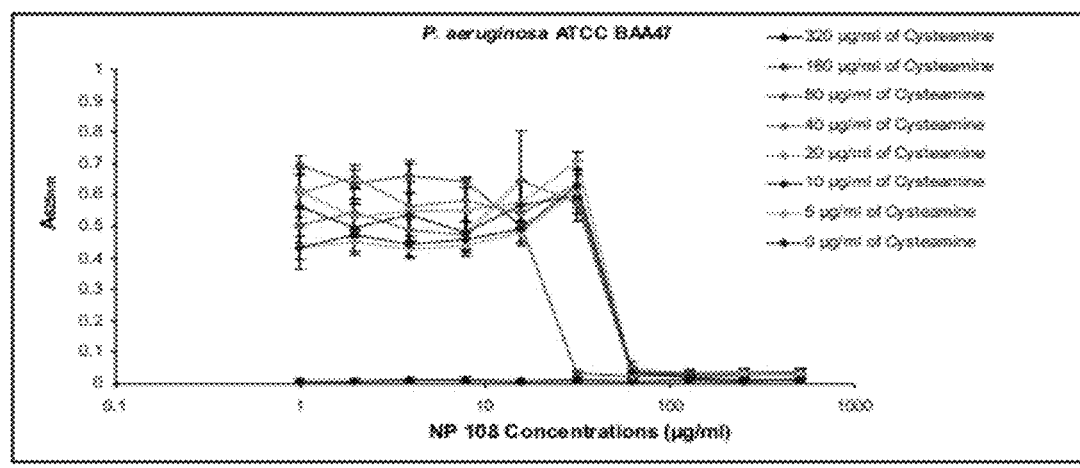
FIG. 2: Antibacterial activity of NP108 and NM001 (cysteamine) combinations against *P. aeruginosa* ATCC BAA-47 planktonic cells
Figure 3:
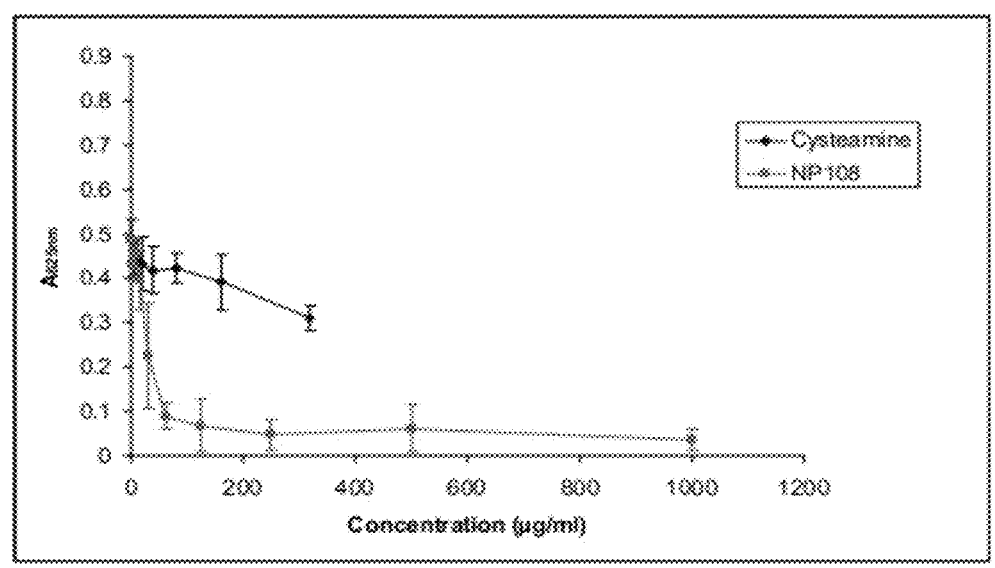
FIG. 3: Antibacterial activity of NP108 and NM001 (cysteamine) against *S. aureus* DSM 11729 planktonic cells

The FIC obtained with those MBEC values ($MBEC_{NP108[alone]}$>500 µg/ml, $MBEC_{NP108[combination]}$=250 µg/ml, $MBEC_{cysteamine[combination]}$=62.5 µg/ml, $MBEC_{cysteamine[alone]}$=>100,00 µg/ml,) was ~0.5, which indicates a synergistic effect between these two antimicrobial agents. This is consistent with the observations made from the activity of NP108/cysteamine combination against the planktonic cells (FIG. 2).

The activity of NP108 and cysteamine against the persister cells was assessed using a fluorescence staining method to determine the relative viability of the cells. The nucleic acid-binding fluorescent molecules used were SYTO9 and PI, which penetrate all bacterial cells (green fluorescence) and membrane-disrupted cells (red fluorescence), respectively. Therefore the ratio green (live)/red (dead) fluorescence emitted gives an indication of the relative viability of the bacterial population and is used to estimate the presence of residual live cells corresponding to persister cells within the biofilm.

Figure 12:
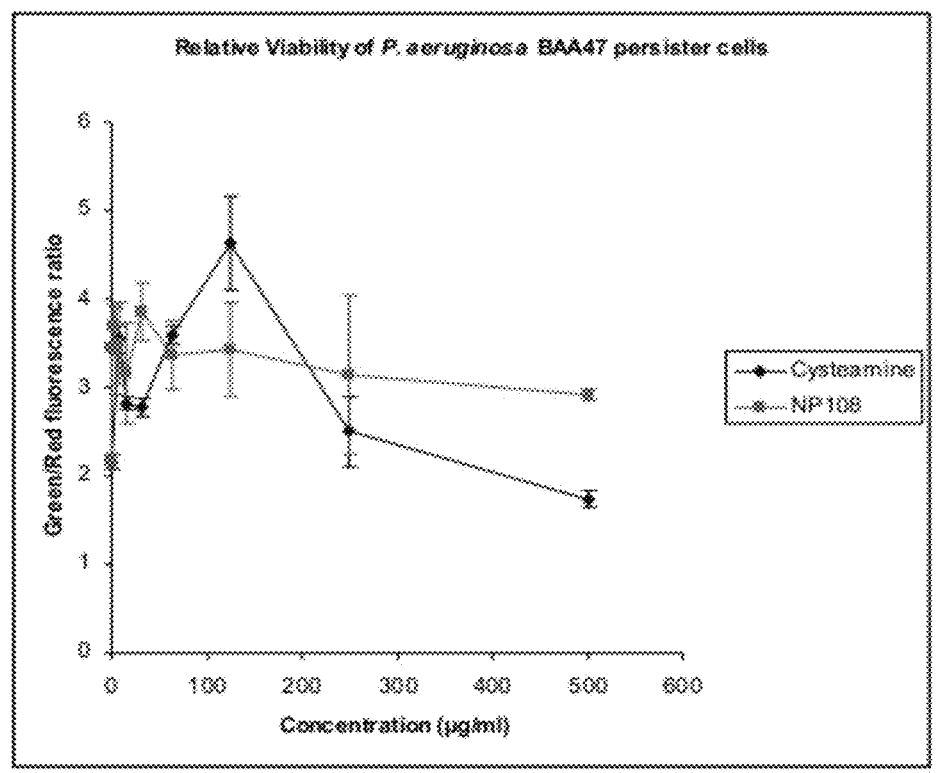
FIG. 12: Antibacterial activity of NP108 and NM001 (cysteamine) against P. aeruginosa ATCC BAA-47 persister cells

FIG. 12 shows that the relative viability of the biofilms treated with either NP108 or cysteamine remained significant, indicating the lack of activity of these compounds against the persister cells of P. aeruginosa ATCC BAA-47.

Figure 13:
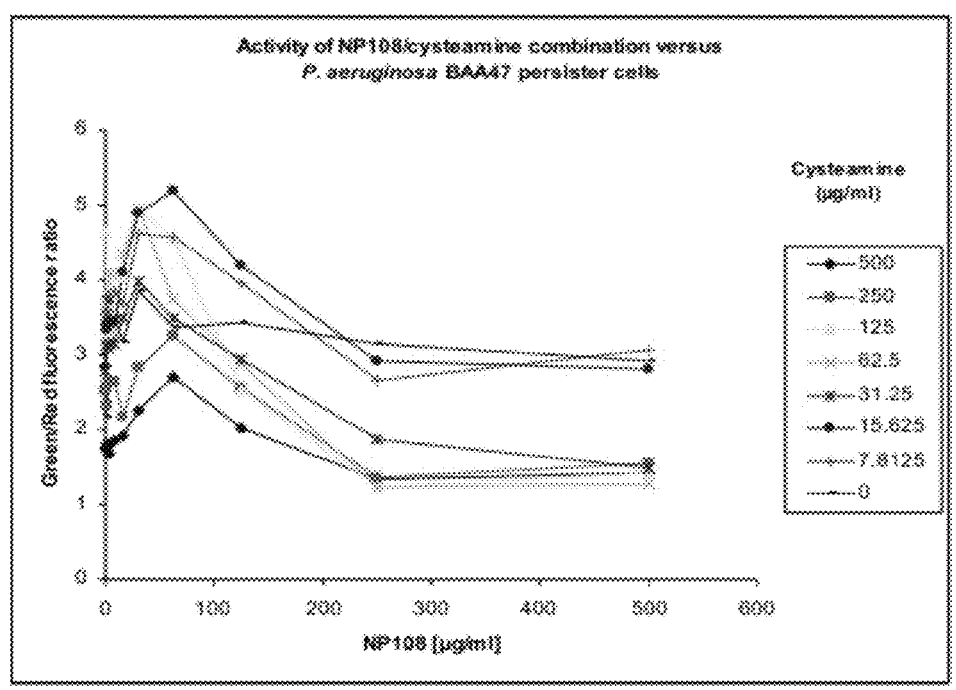
FIG. 13: Antibacterial activity of NP108 and NM001 (cysteamine) combinations against P. aeruginosa ATCC BAA-47 persister cells

FIG. 13 provides evidence that the combination of NP108 and cysteamine showed higher activity against the persister cells of P. aeruginosa ATCC BAA-47 than either compound alone (FIG. 12). The most efficient combinations against those cells were 250-500 µg/ml NP108 and 62.5-500 µg/ml cysteamine. These combinations showed the lowest relative viability within the biofilms. Similar results were obtained with 31.25 µg/ml NP108 and 500 µg/ml cysteamine with only partial inhibition observed with 250 µg/ml cysteamine.

Figure 11:
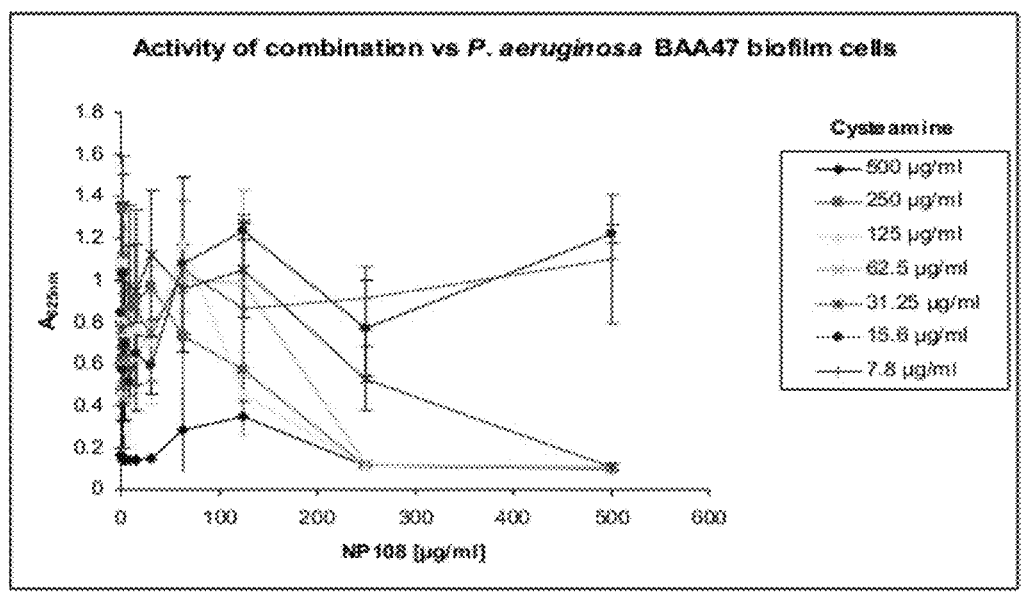
FIG. 11: Antibacterial activity of NP108 and NM001 (cysteamine) combinations against P. aeruginosa ATCC BAA-47 biofilm cells

The activity of these compounds against persister cells shows similarities to the profile of optimum combinations obtained against the biofilm cells (FIG. 11). Moreover, direct microscopic observations of the fluorescently-stained biofilms confirmed the activity of these combinations against the persister cells as no live cells could be observed in the presence of 250-500 µg/ml NP108 and 62.5-500 µg/ml cysteamine (data not shown).

2.2.5 Activity of NP339 and Cysteamine in Combination Against P. aeruginosa

FIG. 14(a)-(d) show the activity of 3 concentrations of NP339: 1 µg/ml, 10 µg/ml and 100 µg/ml in combination with increasing concentrations of cysteamine up to 10 mg/ml against 4 strains of Pseudomonas aeruginosa.

These data clearly demonstrate the increased antimicrobial activity against P. aeruginosa biofilm cells of NP339 in combination with cysteamine. The following figures show examples of the activity of these combinations against persister cells of 2 of these strains.

Figure 16:
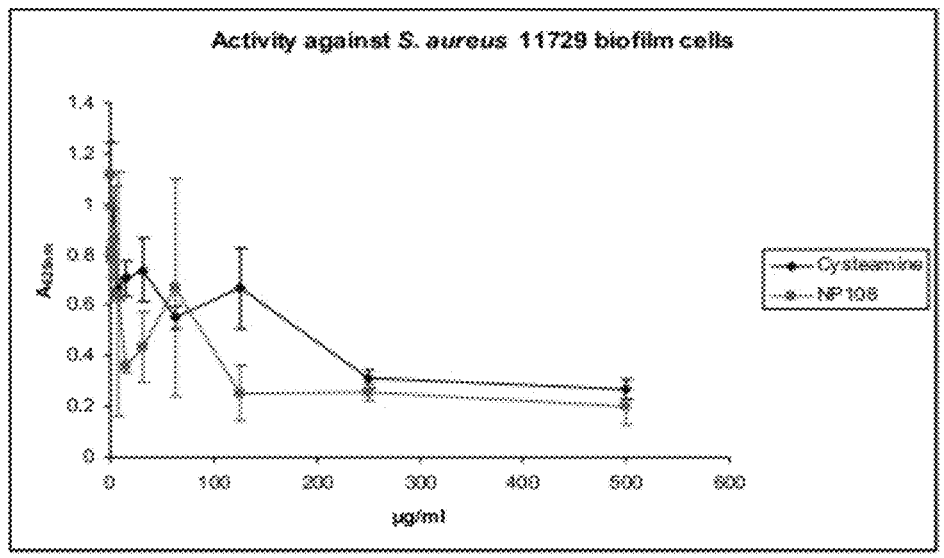
FIG. 16: Antibacterial activity of NP108 and NM001 (cysteamine) against S. aureus DSM 11729 biofilm cells

FIG. 16 shows the activity of NP108 and cysteamine against S. aureus DSM 11729 biofilm cells. The MBEC for cysteamine was 250 µg/ml, whereas NP108 inhibited the growth of those cells at 125 µg/ml.

Figure 4:
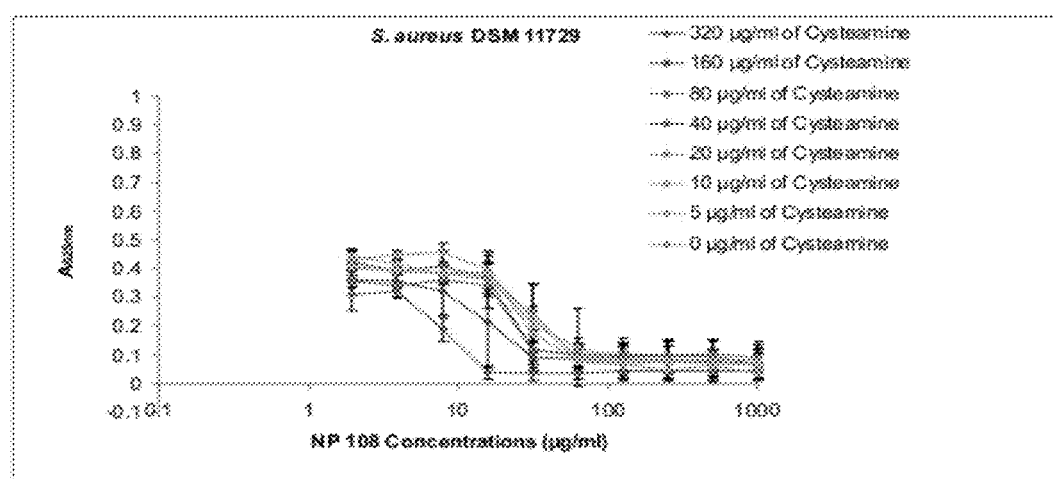
FIG. 4: Antibacterial activity of NP108 and NM001 (cysteamine) combinations against *S. aureus* DSM 11729 planktonic cells
Figure 17:
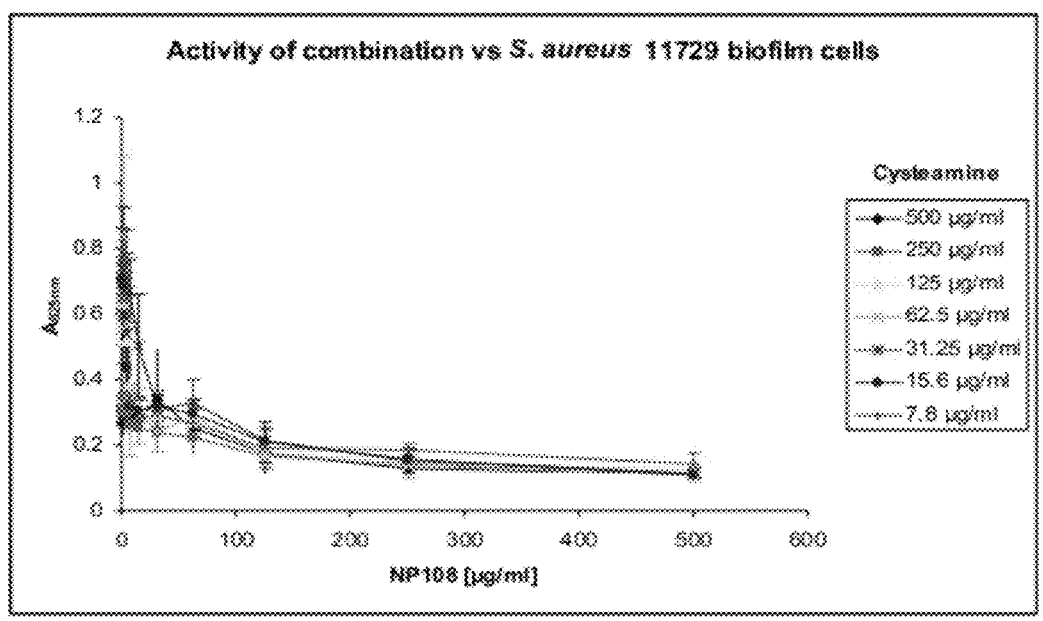
FIG. 17: Antibacterial activity of NP108 and NM001 (cysteamine) combinations against S. aureus DSM 11729 biofilm cells

The combination of NP108 and cysteamine showed complete inhibition of bacterial growth in the presence of 31.25 µg/ml NP108 and 62.5 µg/ml cysteamine and partial inhibition with lower concentrations of either compound (FIG. 17). Hence, the FIC obtained with those MBEC ($MBEC_{NP108[alone]}$ 125 µg/ml, $MBEC_{NP108[combination]}$= 31.25 µg/ml, $MBEC_{cysteamine[alone]}$=250 µg/ml, $MBEC_{cysteamine[combination]}$=62.5 µg/ml) was 0.5 thereby indicating a synergistic effect between these two antimicrobial agents against biofilm of these Gram-positive bacteria. Similar results were observed for Gram-negative bacterial biofilm (FIG. 11). This is also consistent with the observations made from the activity of NP108/cysteamine combination against the planktonic cells of S. aureus DSM 11729 (FIG. 4).

Figure 18:
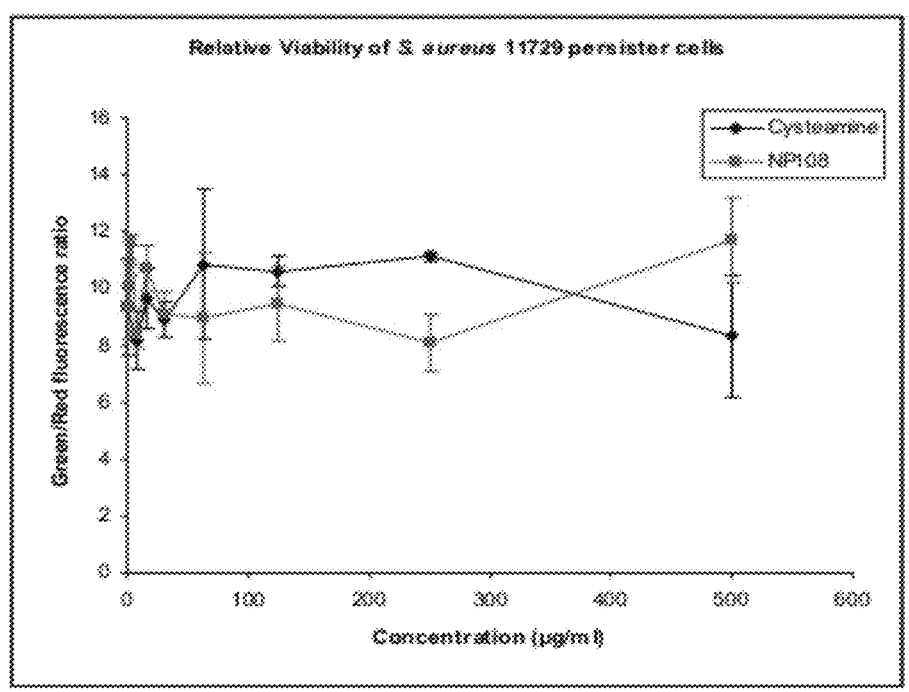
FIG. 18: Antibacterial activity of NP108 and NM001 (cysteamine) against S. aureus DSM 11729 persister cells

Similarly to the lack of activity observed against P. aeruginosa ATCC BAA-47 persister cells (FIG. 12), the relative viability of the S. aureus DSM 11729 biofilms treated with either NP108 or cysteamine remained significant, indicating the lack of activity of these compounds at low concentrations against the persister cells of these Gram-positive bacteria (FIG. 18).

Figure 19:
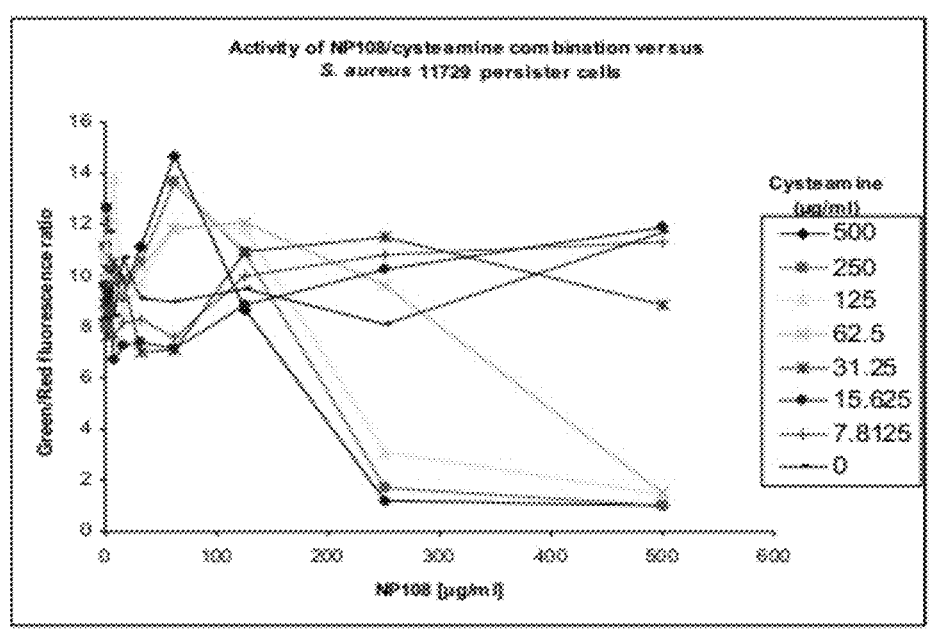
FIG. 19: Antibacterial activity of NP108 and NM001 (cysteamine) combinations against S. aureus DSM 11729 persister cells
Figure 22:
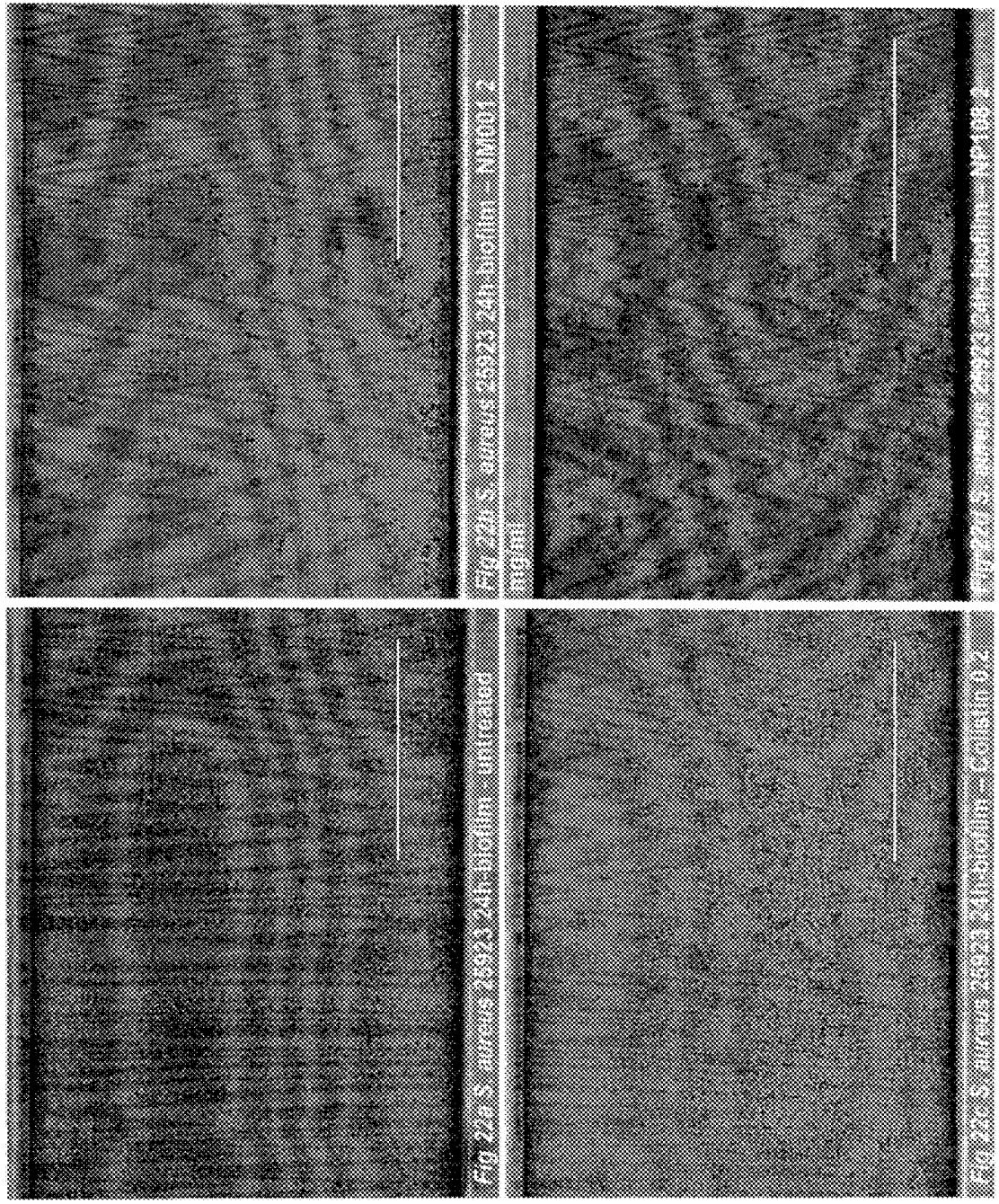
FIG. 22a: untreated control S. aureus biofilm after 24 hours
FIG. 22b: S. aureus biofilm 24 hours following treatment with NM001 (cysteamine) at 2 mg/ml
FIG. 22c: S. aureus biofilm 24 hours following treatment with Colistin at 0.2 mg/ml
FIG. 22d: S. aureus biofilm 24 hours following treatment with peptide NP108 at 2 mg/ml
Figure 23:
FIG. 23a: untreated control S. aureus biofilm after 24 hours
FIG. 23b: S. aureus biofilm 24 hours following treatment with NM001 (cysteamine) at 2 mg/ml
FIG. 23c: S. aureus biofilm 24 hours following treatment with Colistin at 0.2 mg/ml
FIG. 23d: S. aureus biofilm 24 hours following treatment with peptide NP108 at 2 mg/ml
Figure 24:
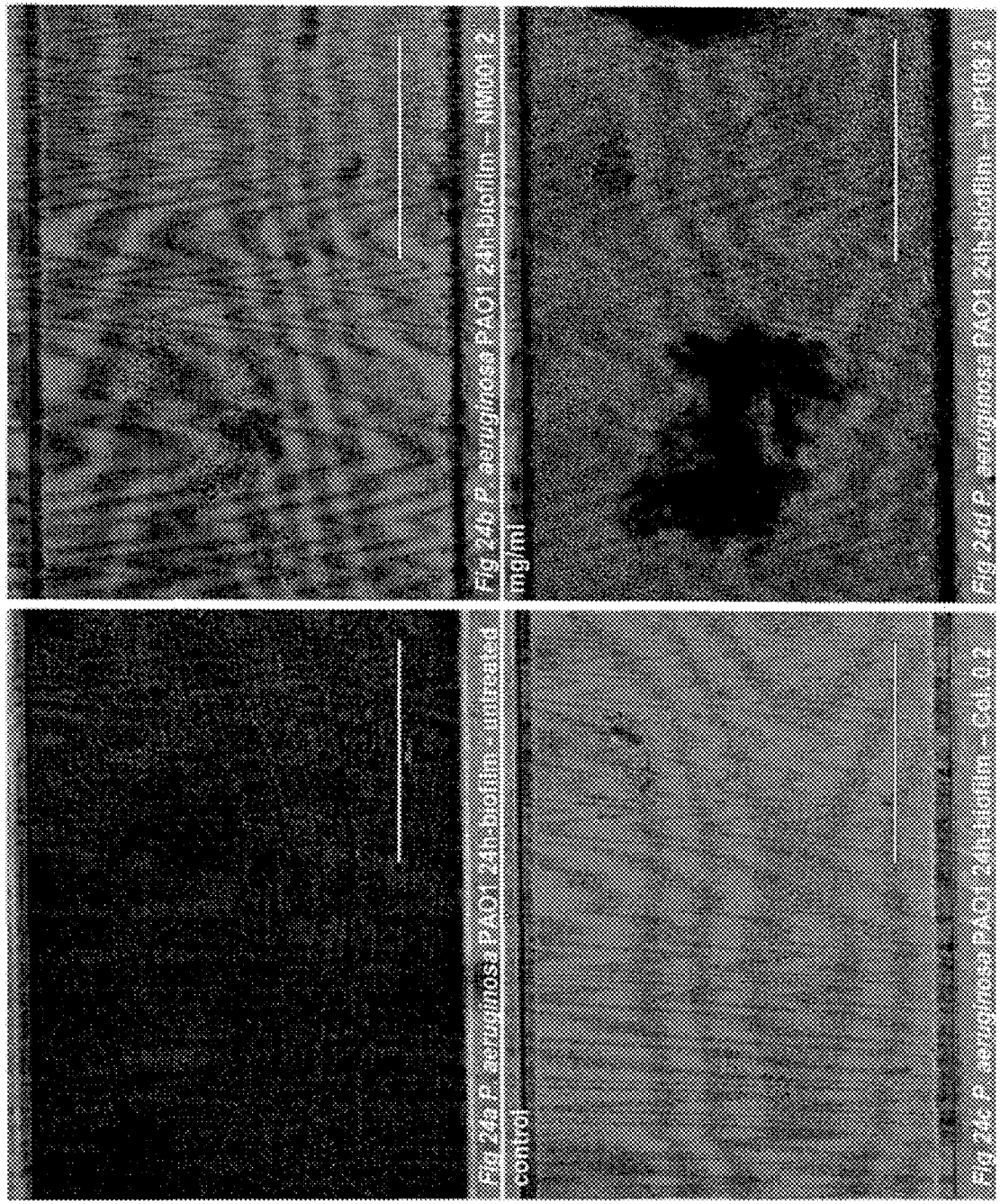
FIG. 24a: untreated control P. aeruginosa biofilm after 24 hours
FIG. 24b: P. aeruginosa biofilm 24 hours following treatment with NM001 (cysteamine) at 2 mg/ml
FIG. 24c: P. aeruginosa biofilm 24 hours following treatment with Colistin at 0.2 mg/ml
FIG. 24d: P. aeruginosa biofilm 24 hours following treatment with peptide NP108 at 2 mg/ml
Figure 25:
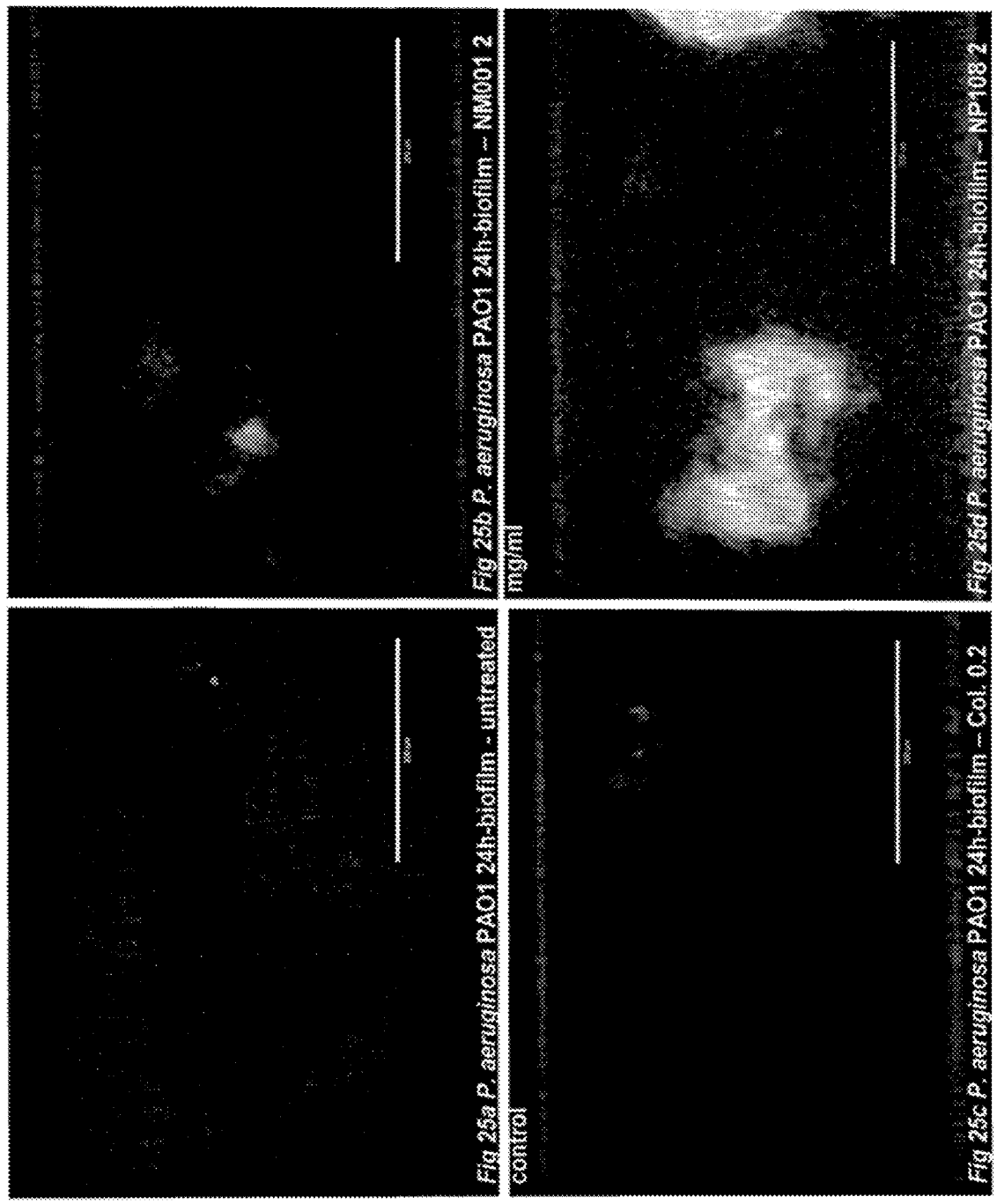
FIG. 25a: untreated control P. aeruginosa biofilm after 24 hours
FIG. 25b: P. aeruginosa biofilm 24 hours following treatment with NM001 (cysteamine) at 2 mg/ml
FIG. 25c: P. aeruginosa biofilm 24 hours following treatment with Colistin at 0.2 mg/ml
FIG. 25d: P. aeruginosa biofilm 24 hours following treatment with peptide NP108 at 2 mg/ml
Figure 26:
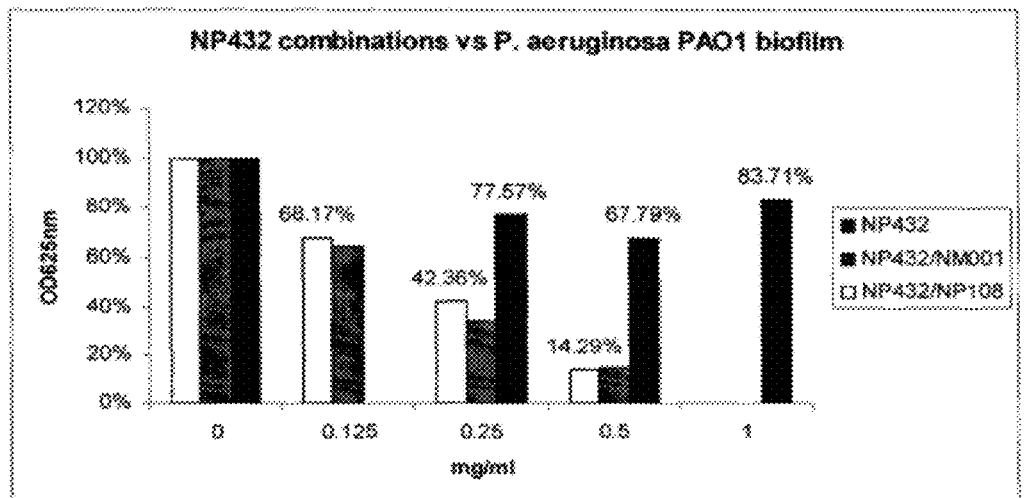
FIG. 26: Activity of NP432 alone and in combination with NM001 (cysteamine) or in combination with NP108 against P. aeruginosa PAO1 biofilm
Figure 27:
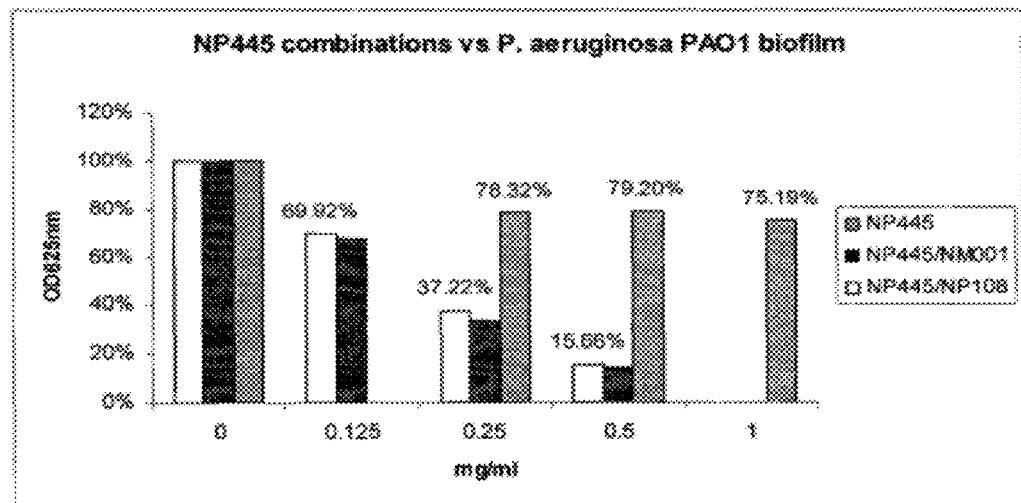
FIG. 27: Activity of NP445 alone and in combination with NM001 (cysteamine) or in combination with NP108 against P. aeruginosa PAO1 biofilm
Figure 28:
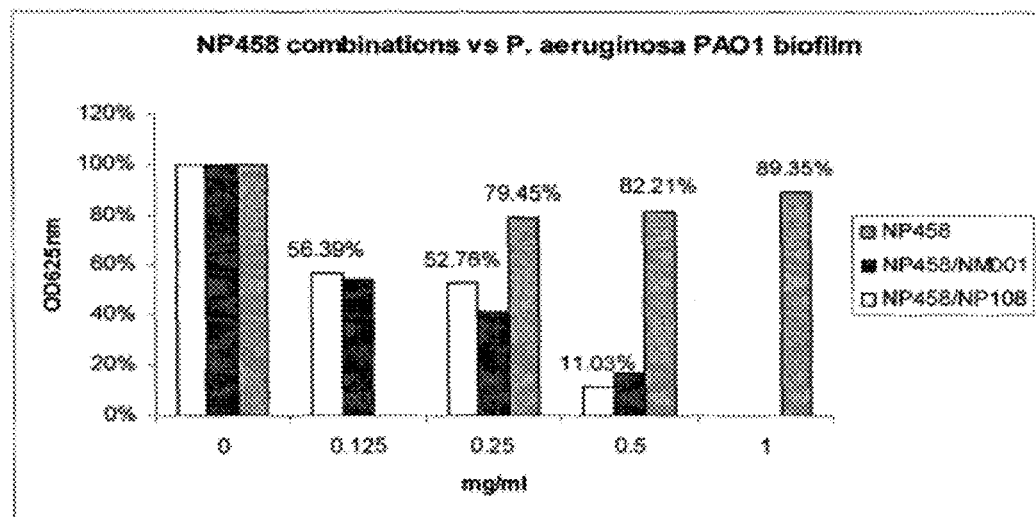
FIG. 28: Activity of NP458 alone and in combination with NM001 (cysteamine) or in combination with NP108 against P. aeruginosa PAO1 biofilm
Figure 29:
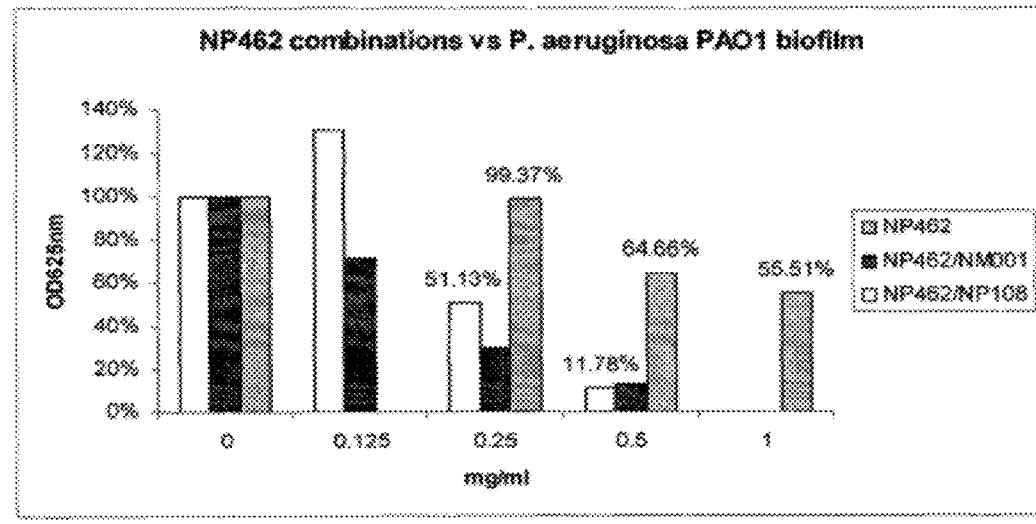
FIG. 29: Activity of NP462 alone and in combination with NM001 (cysteamine) or in combination with NP108 against P. aeruginosa PAO1 biofilm
Figure 30:
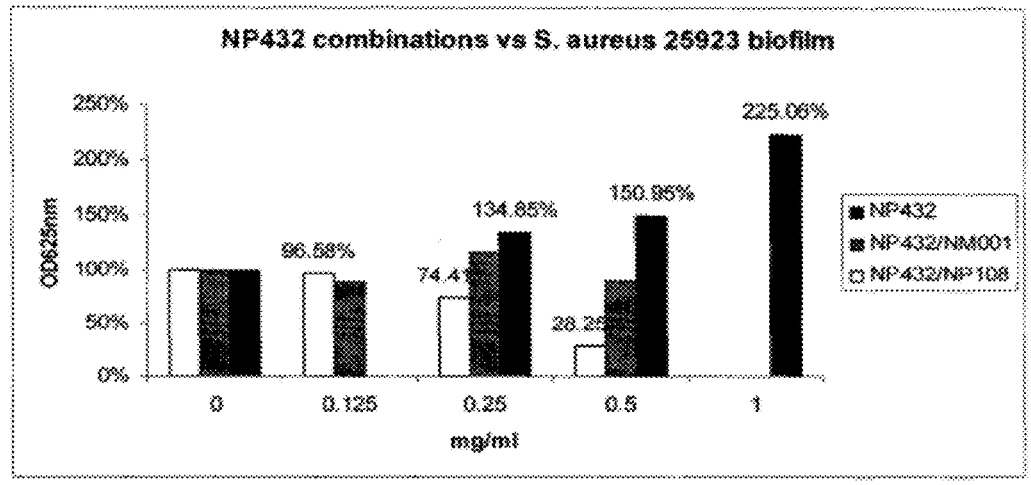
FIG. 30: Activity of NP432 alone and in combination with NM001 (cysteamine) or in combination with NP108 against S. aureus ATCC25923 biofilm
Figure 31:
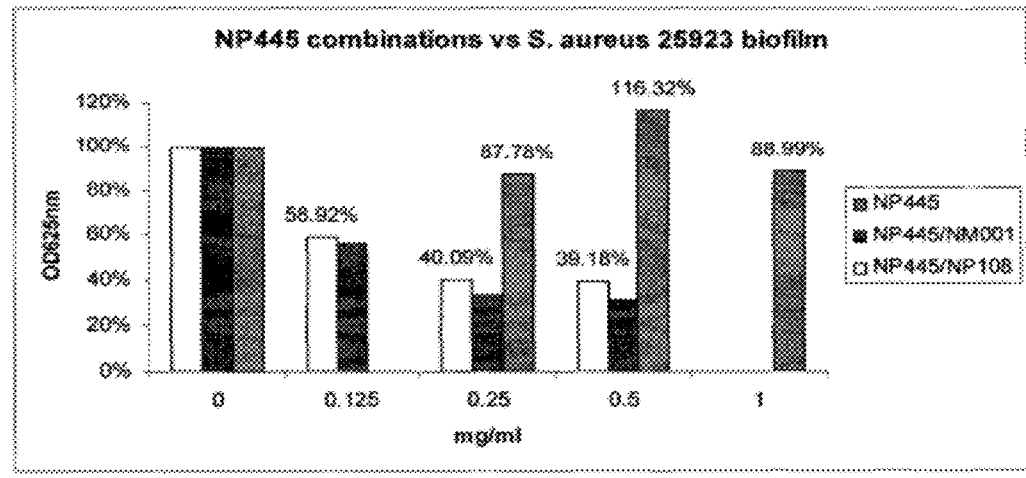
FIG. 31: Activity of NP445 alone and in combination with NM001 (cysteamine) or in combination with NP108 against S. aureus ATCC25923 biofilm
Figure 32:
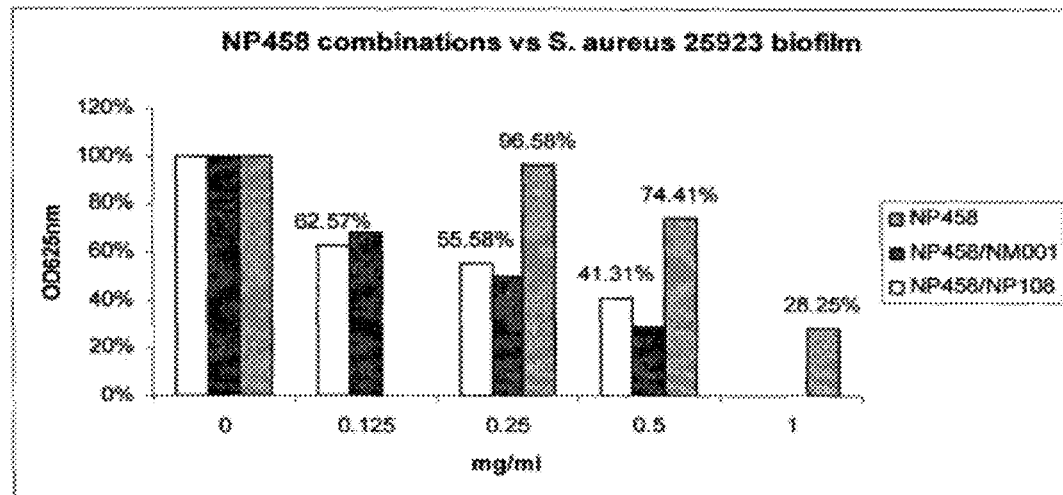
FIG. 32: Activity of NP458 alone and in combination with NM001 (cysteamine) or in combination with NP108 against S. aureus ATCC25923 biofilm
Figure 33:
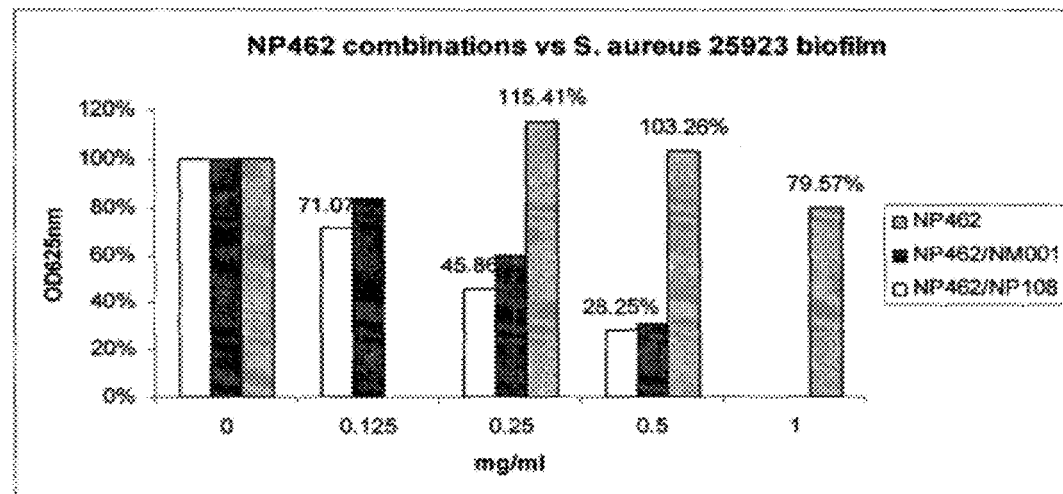
FIG. 33: Activity of NP462 alone and in combination with NM001 (cysteamine) or in combination with NP108 against S. aureus 25923 biofilm Table 1: Summary of the activity of the tested antimicrobial agents against the Gram-negative P. aeruginosa strains and the Gram-positive Staphylococcus spp.

The combination of NP108 and cysteamine showed higher activity against the persister cells of S. aureus DSM 11729 than either compound alone (FIG. 19). The most efficient combinations against those cells were 250-500 µg/ml NP108 and 125-250 µg/ml cysteamine. These combinations showed the lowest relative viability within the biofilms. Similar results were obtained with 62.5 µg/ml NP108 and 500 µg/ml cysteamine. Combinations with lower concentrations of either compound showed high relative viability within the biofilms.

Unlike the Gram-negative persister cells, direct microscopic observations of the fluorescently-stained S. aureus DSM 11729 biofilms indicated the presence of residual live cells at the highest combined concentrations of NP108 and cysteamine (data not shown).

Table 1 provides a summary of the activity of the short arginine peptides NP339, NP341, the poly-L-lysine NP108, cysteamine and the combination of NP108 with cysteamine against a Gram-positive and Gram-negative bacteria.

TABLE 1

Summary of the activity of the tested antimicrobial agents against the Gram-negative P. aeruginosa strains and the Gram-positive Staphylococcus spp.

|  |  | P. aeruginosa strains (7) | Staphylococcus spp (4) |
|---|---|---|---|
| MIC (µg/ml) | NP108 | 31.25-500 | 16-125 |
|  | NP339 | 62.5 | 4-128 |
|  | NP341 | 31.25 | 250 |
|  | Cysteamine | 300-2,500 | 300-625 |
|  | NP108/Cysteamine | 31.25/160 | 31.25/40 |
|  | NP108/ | 1 | 0.6 |

TABLE 1-continued

Summary of the activity of the tested antimicrobial agents against the Gram-negative *P. aeruginosa* strains and the Gram-positive *Staphylococcus* spp.

| | | | *P. aeruginosa* strains (7) | *Staphylococcus* spp (4) |
|---|---|---|---|---|
| FIC: | | Cysteamine | | |
| | MBEC (μg/ml) | NP108 | 250->500 | 125-250 |
| | | NP339 | >5,000 | 156-625 |
| | | NP341 | >5,000 | 625->5,000 |
| | | Cysteamine | >5,000 | >25,000 |
| | | NP108/Cysteamine | 125/125-250/62.5 | 31.25/62.5-125/125 |
| | | NP108/Cysteamine | ≤0.75 | 0.5-1 |
| FIC: | | Cysteamine | | |
| | Persisters (μg/ml) | NP108 | 250->500 | >500 |
| | | NP339 | 625 | 625->5,000 |
| | | NP341 | 625 | 625->5,000 |
| | | Cysteamine | 500-6,250 | 6,250-12,500 |
| | | NP108/Cysteamine | 62.5/250-250/62.5 | >250/>250 |
| | | NP108/Cysteamine | 0.75-1 | ≤0.5 |
| FIC: | | Cysteamine | | |

The number into brackets indicates the maximum number of strains tested.
MIC: minimum inhibition concentration;
MBEC: minimum biofilm eradication concentration;
FIC: fractional inhibitory concentration.
Notes:
appendix 1 shows the MIC of the tested short arginine antimicrobials against *Staphylococcus aureus* DSM 11729.
appendix 2 shows the activity of the mucolytic agents cysteamine and N-acetylcysteine in combination with NP341 against *P. aeruginosa* ATCC27853.

Appendix 1

The data (not shown) demonstrates the activity of short linear arginine peptides over a 48-h period against planktonic cells of methicillin-resistant *S. aureus* (MRSA) DSM 11729. The range of concentrations tested as shown in the legends is in mg/ml. The data (not shown) demonstrates the activity of short linear arginine peptides over a 48-h period against planktonic cells of methicillin-resistant *S. aureus* (MRSA) DSM 11729. The time course activity demonstrates that bacterial growth inhibition is associated with the dose of antimicrobial and to the time of exposure to the cells. Complete bactericidal activity was observed for NP339, NP 340 and NP352 at concentrations above 0.5 mg/ml for the 48-h period; 0.125 and 0.25 mg/ml showed complete inhibition for at least 24 h, and lower concentrations such as 0.06 and 0.03 mg/ml showed complete inhibition for at least 20 h and 15 h, respectively. Similar results were obtained with NP341, except that 0.25 mg/ml showed complete inhibition for the 48-h period.

Appendix 2

In combination with 3-6 mg/ml of N-acetylcysteine, however, only 205 μg/ml of NP341 are needed to reach the MBEC (FIG. 20a). Similar increased activity for the combination of these 2 compounds was observed against persister cells: 1024 μg/ml NP341+3128 μg/ml N-acetylcysteine inhibited approximately 75% of the persister cells, which is a much higher inhibition than that obtained with either of the two compounds alone (FIG. 20b).

The combination of cysteamine or N-acetylcysteine with NP341 shows increased antibacterial activity compared to the activity of either compound alone. The MBEC of NP341 alone against *P. aeruginosa* ATCC27853 was more than 2 mg/ml and more than 100 mg/ml for cysteamine (FIG. 21a). This indicates that there is no cooperative effect between the two compounds against the biofilm cells of *P. aeruginosa* ATCC27853. However, such cooperation was observed against the persister cells: 205 μg/ml NP341+3 mg/ml cysteamine inhibit approximately 75% of the persister cells, which is much higher than any of the two compounds alone (FIG. 21b).

When used in combination with NP339, we observed that the addition of cysteamine even in small amounts helps reducing the MBEC values of NP339 (FIG. 14a-d). More interestingly, the combination of NP339 and cysteamine also showed increased activity against persister cells of *P. aeruginosa* DSM1128 and *P. aeruginosa* BAA-47 (FIG. 15a-b).

The invention claimed is:

1. A method of treating a bacterial infection or disease comprising administering a therapeutically effective amount of an antimicrobial peptide comprising amino acids according to the formula I:

$$((X)_l(Y)_m)_n \tag{I}$$

wherein l and m are integers from 1 to 10; n is an integer from 1 to 10; X and Y, which may be the same or different, are independently selected from a hydrophobic and a cationic amino acid and a therapeutically effective amount of cysteamine.

2. The method according to claim 1, wherein infection, or disease, is selected from the group consisting of skin and wound infections, middle-ear infections, gastrointestinal tract infections, peritoneal membrane infections, urogenital tract infections, oral soft tissue infections, formation of dental plaque, eye infections, endocarditis, infections in cystic fibrosis, and infections of indwelling medical devices.

3. A method of treating a bacterial infection by prophylaxis or therapy comprising the sequential or combined administration in a therapeutically effective amount of:
   a first antibiofilm agent; and
   a second antibiofilm agent different from the first antibiofilm agent;
wherein the first antibiofilm agents is an antimicrobial peptide and the second antibiofilm agent is cysteamine wherein the antimicrobial peptide comprises amino acids according to formula I:

$$((X)_l(Y)_m)_n \tag{I}$$

wherein l and m are integers from 1 to 10, n is an integer from 1 to 10; and X and Y, which may be the same or different, are independently selected from a hydrophobic and a cationic amino acid.

4. The method according to claim 3 wherein the bacterial infection is a topical infection.

5. The method according to claim 4 wherein the topical infection is selected from a wound, ulcer and lesion.

6. The method according to claim 3 wherein the bacterial infection is an oral infection.

7. The method according to claim 6 wherein the oral infection is selected from gingivitis, periodontitis and mucositis.

8. The method according to claim 3 wherein the bacterial infection is a systemic infection.

9. The method according to claim 8 wherein the systemic infection is a mucosal infection.

10. The method according to claim 9 wherein the mucosal infection is a gastrointestinal, urogenital or respiratory infection.

11. The method according to claim 9 wherein the mucosal infection is cystic fibrosis.

12. A method of treating a bacterial infection in a subject in need of said treating, comprising administering to said subject an amount of cysteamine effective to treat said infection.

13. The method according to claim 1, wherein l and m are integers from 1 to 5.

14. The method according to claim 3, wherein l and m are integers from 1 to 5.

15. The method according to claim 14, wherein the bacterial infection is respiratory infection.

* * * * *